(12) United States Patent  
Jerauld

(10) Patent No.: US 9,189,021 B2  
(45) Date of Patent: Nov. 17, 2015

(54) WEARABLE FOOD NUTRITION FEEDBACK SYSTEM

(71) Applicant: MICROSOFT TECHNOLOGY LICENSING, LLC, Redmond, WA (US)

(72) Inventor: Robert Jerauld, Kirkland, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 13/689,293

(22) Filed: Nov. 29, 2012

(65) Prior Publication Data

US 2014/0147829 A1    May 29, 2014

(51) Int. Cl.  
*G09B 25/00* (2006.01)  
*G06F 1/16* (2006.01)  
*G06F 3/01* (2006.01)  
*G06F 19/00* (2011.01)  
*G09B 19/00* (2006.01)

(52) U.S. Cl.  
CPC ............... *G06F 1/163* (2013.01); *G06F 3/011* (2013.01); *G06F 3/013* (2013.01); *G06F 19/3475* (2013.01); *G09B 19/0092* (2013.01)

(58) Field of Classification Search  
CPC ........................................................ G09B 25/00  
USPC ........................................................ 434/430  
See application file for complete search history.

(56) References Cited

U.S. PATENT DOCUMENTS

| | | | |
|---|---|---|---|
| 6,030,342 A | 2/2000 | Amano et al. | |
| 6,513,532 B2 | 2/2003 | Mault et al. | |
| 6,694,182 B1 | 2/2004 | Yamazaki et al. | |
| 7,693,702 B1 | 4/2010 | Kerner et al. | |
| 8,432,489 B2 | 4/2013 | Arseneau et al. | |
| 2004/0162702 A1 | 8/2004 | Pandipati et al. | |
| 2005/0113649 A1 | 5/2005 | Bergantino | |
| 2006/0230108 A1* | 10/2006 | Tatsuta et al. | 709/204 |
| 2006/0230123 A1 | 10/2006 | Simmons et al. | |
| 2007/0088746 A1 | 4/2007 | Baker | |
| 2007/0173705 A1 | 7/2007 | Teller et al. | |
| 2007/0218174 A1 | 9/2007 | Hanamatsu et al. | |
| 2007/0282176 A1 | 12/2007 | Shimada et al. | |

(Continued)

FOREIGN PATENT DOCUMENTS

AU    2012201615 A1    4/2012

OTHER PUBLICATIONS

Foodsnap!, "How We Do It", http://www.foodsnap.mobi/#how-we-do-it, Oct. 16, 2012.

(Continued)

*Primary Examiner* — Xuan Thai  
*Assistant Examiner* — Robert P Bullington  
(74) *Attorney, Agent, or Firm* — Dan Choi; Judy Yee; Micky Minhas

(57) ABSTRACT

A see-through, head mounted display and sensing devices cooperating to provide feedback on food items detected in the device field of view. Feedback can include warnings based on personal wearer needs, general nutrition information, food consumption tracking and social interactions. The system includes one or more processing devices in communication with display and the sensors which identify food items proximate to the apparatus, determine feedback information relevant to a wearer of the apparatus; and render feedback information in the display.

20 Claims, 21 Drawing Sheets

(56) References Cited

U.S. PATENT DOCUMENTS

| | | | |
|---|---|---|---|
| 2008/0073430 | A1 | 3/2008 | Sickenius |
| 2008/0082465 | A1 | 4/2008 | Meijer et al. |
| 2009/0144081 | A1 | 6/2009 | Harlan |
| 2009/0176526 | A1 | 7/2009 | Altman |
| 2009/0265381 | A1 | 10/2009 | Canu et al. |
| 2010/0199232 | A1 | 8/2010 | Mistry et al. |
| 2010/0238161 | A1 | 9/2010 | Varga et al. |
| 2010/0257252 | A1 | 10/2010 | Dougherty et al. |
| 2011/0112904 | A1 | 5/2011 | Stupp |
| 2011/0218839 | A1 | 9/2011 | Shamaiengar |
| 2011/0221656 | A1 | 9/2011 | Haddick et al. |
| 2011/0221793 | A1 | 9/2011 | King, III et al. |
| 2011/0270135 | A1 | 11/2011 | Dooley et al. |
| 2011/0318717 | A1 | 12/2011 | Adamowicz |
| 2012/0005222 | A1 | 1/2012 | Bhagwan et al. |
| 2012/0053426 | A1 | 3/2012 | Webster et al. |
| 2012/0072302 | A1 | 3/2012 | Chen et al. |
| 2012/0178065 | A1* | 7/2012 | Naghavi et al. ............... 434/236 |
| 2012/0179665 | A1* | 7/2012 | Baarman et al. .............. 707/709 |
| 2012/0229624 | A1 | 9/2012 | Calman et al. |
| 2012/0233002 | A1 | 9/2012 | Abujbara |
| 2012/0242698 | A1 | 9/2012 | Haddick et al. |
| 2013/0038510 | A1 | 2/2013 | Brin et al. |
| 2013/0044042 | A1 | 2/2013 | Olsson et al. |
| 2013/0085345 | A1* | 4/2013 | Geisner et al. ................ 600/300 |

OTHER PUBLICATIONS

"A High-Tech Gadget that Once Helped the Biggest Loser Contestants Monitor Weight Loss", Retrieved on: Jul. 30, 2012, Available at: http://www.dietsinreview.com/diets/body-bugg/.

Novak, David, "Bodybugg® 3rd Generation Here-Now Lighter, Thinner, Smaller and Offers Wristwatch Digital Display", Published on: Dec. 3, 2010, Available at: http://www.24hourfitness.com/shop/learn/GadgetGUY.html.

Adolphs, Ralph, "Recognizing Emotion From Facial Expressions: Psychological and Neurological Mechanisms", Behavioral and Cognitive Neuroscience Reviews, vol. 1, No. 1, Mar. 2002, pp. 21-62.

International Search Report & the Written Opinion of the International Searching Authority dated Mar. 7, 2014, PCT Application No. PCT/US2013/072488.

Välkkynen, et al., "Mobile Augmented Reality for Retail Environments", In Mobile HCI Workshop on Mobile Interaction in Retail Environments, Aug. 30, 2011, 4 pages.

Joutou, Taichi, et al., "A Food Image Recognition System With Multiple Kernel Learning," 16th IEEE International Conference on Image Processing, Nov. 2009, 4 pages.

Winlock, Tess, et al., "Toward Real-Time Grocery Detection for the Visually Impaired," IEEE Computer Society Conference on Computer Vision and Pattern Recognition Workshops, Jun. 2010, 8 pages.

Office Action dated Feb. 11, 2014, U.S. Appl. No. 13/436,526, filed Mar. 30, 2012.

Response to Office Action dated May 12, 2014, U.S. Appl. No. 13/436,526, filed Mar. 30, 2012.

Notice of Allowance dated Jun. 20, 2014, U.S. Appl. No. 13/436,526, filed Mar. 30, 2012.

Office Action dated Oct. 10, 2014, U.S. Appl. No. 13/436,526, filed Mar. 30, 2012, 12 pages.

Response to Office Action dated Jan. 12, 2015, U.S. Appl. No. 13/436,526, filed Mar. 30, 2012, 11 pages.

Notice of Allowance dated Feb. 13, 2015, U.S. Appl. No. 13/436,526, filed Mar. 30, 2012, 16 pages.

Corrected Notice of Allowance dated Mar. 2, 2015, U.S. Appl. No. 13/436,526, filed Mar. 30, 2012, 6 pages.

* cited by examiner

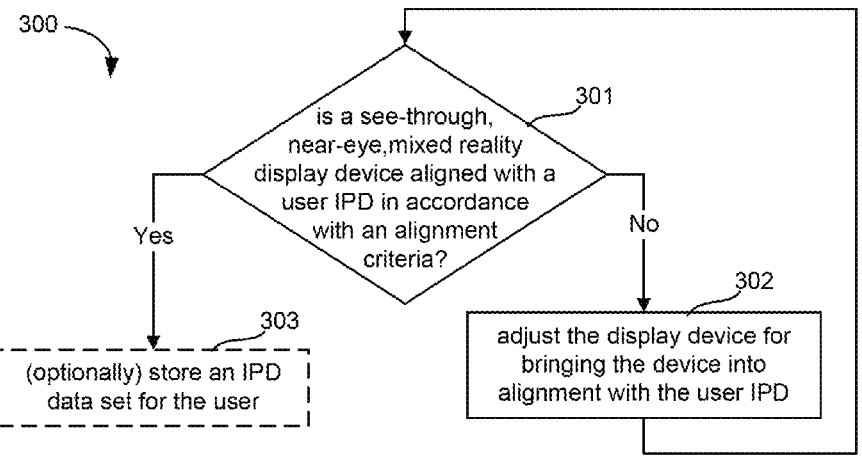
FIG. 3A
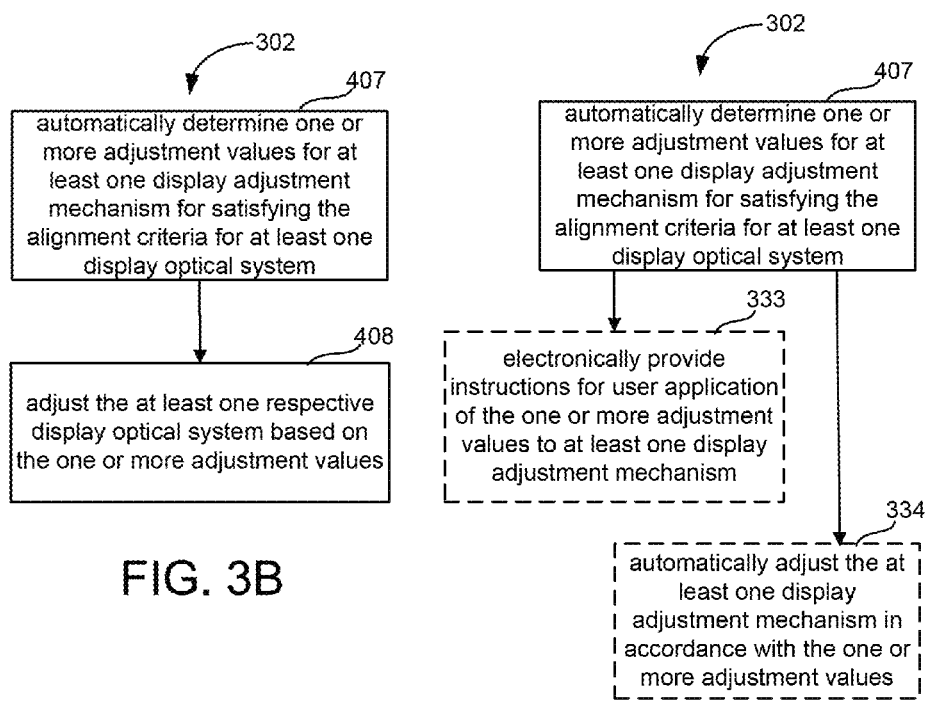
FIG. 3B
FIG. 3C

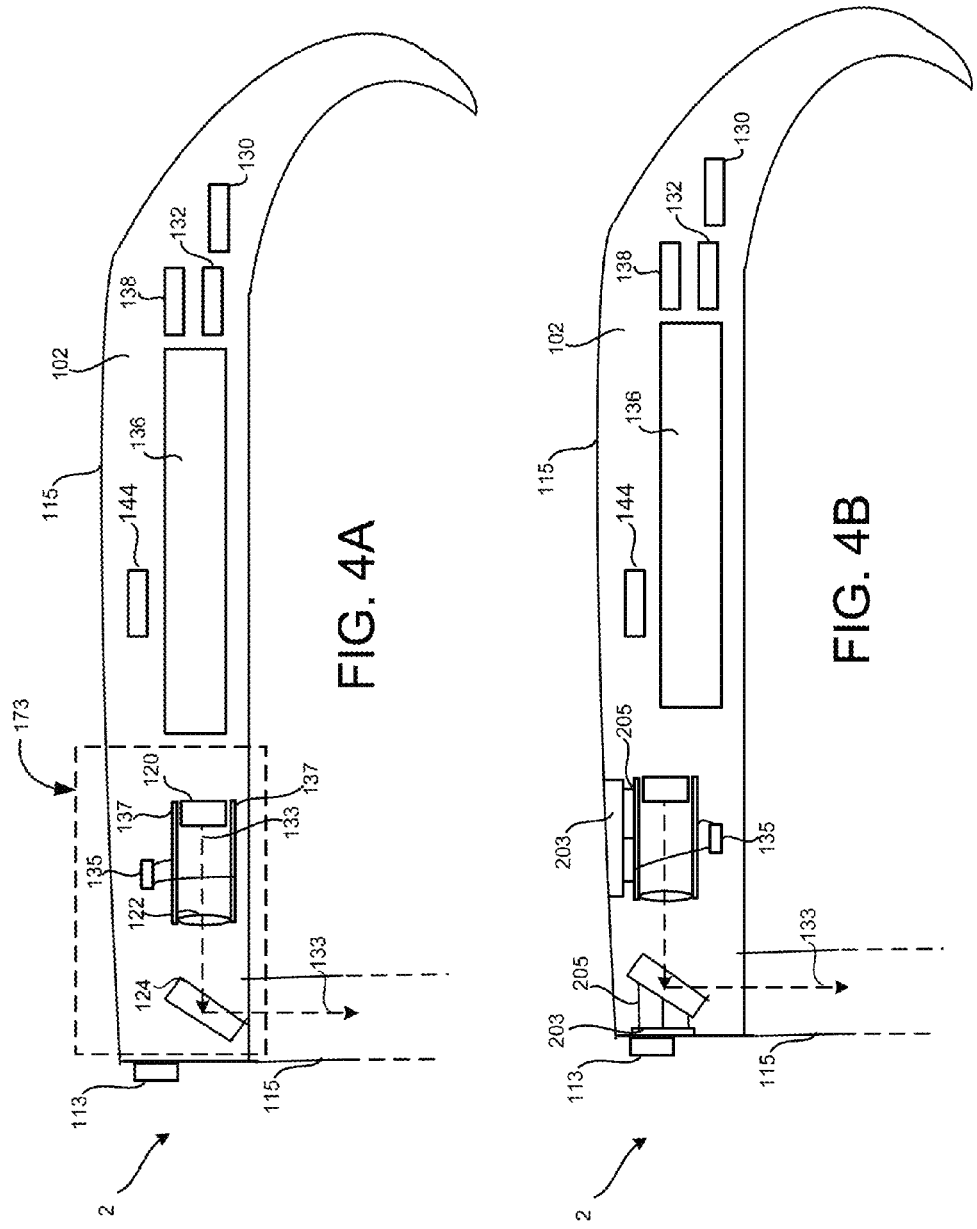

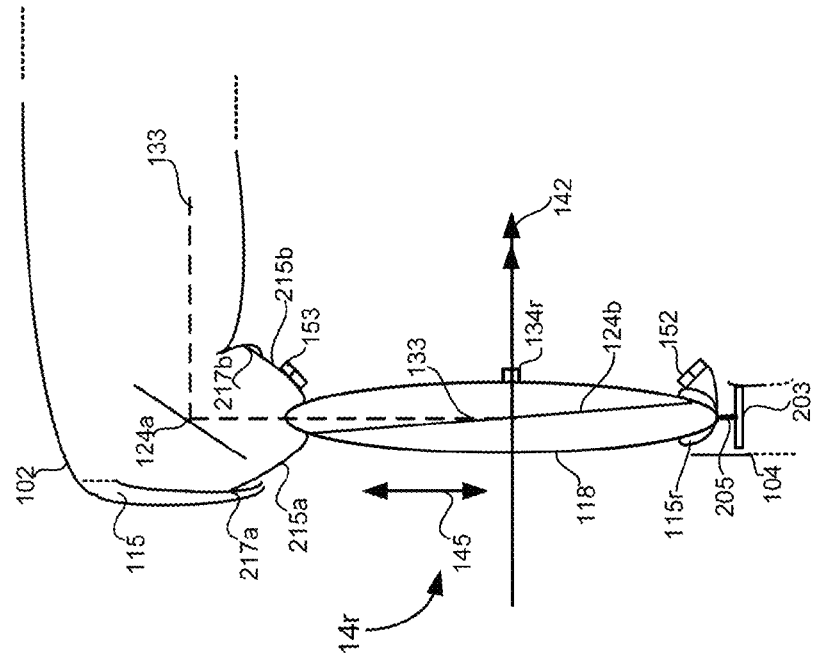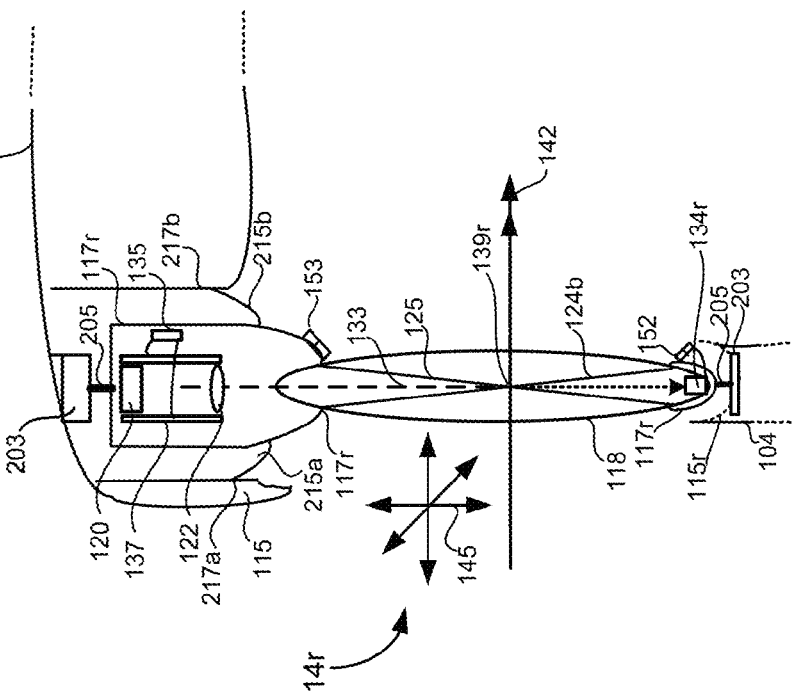

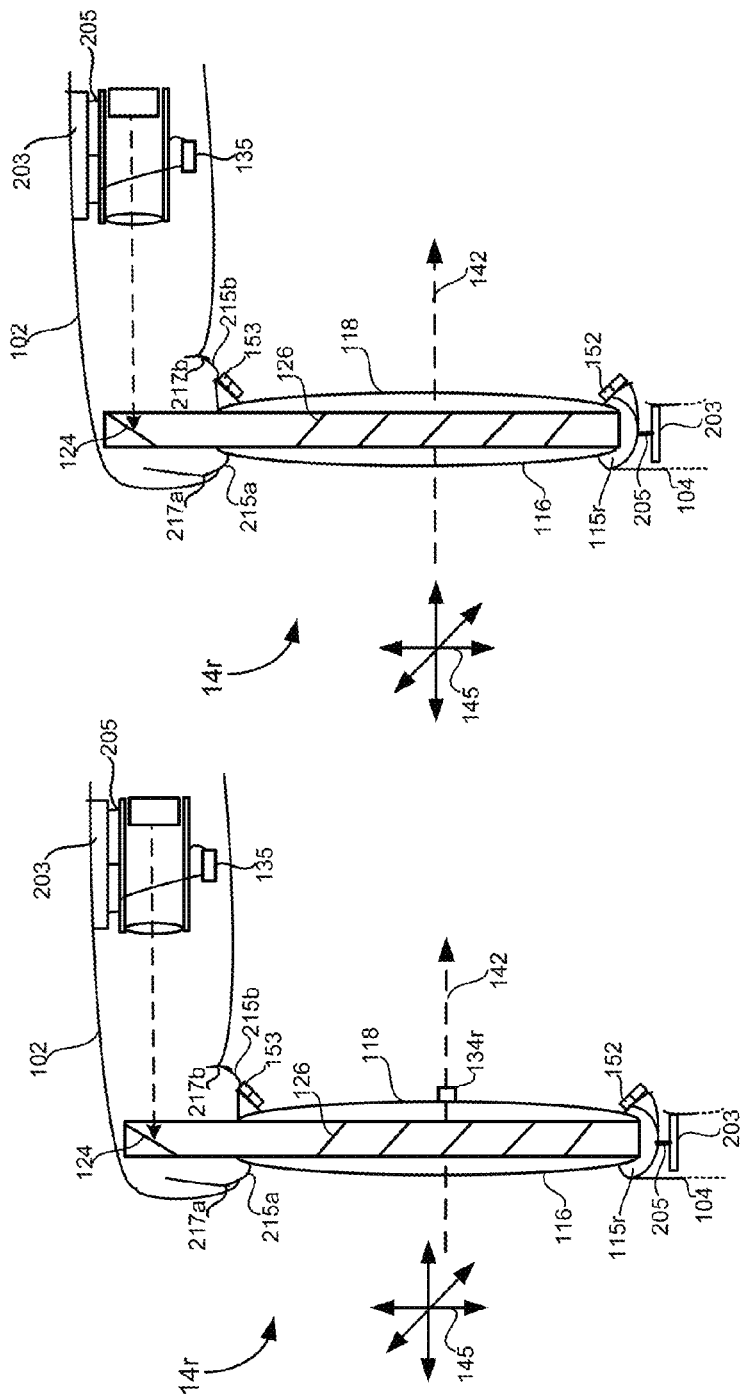

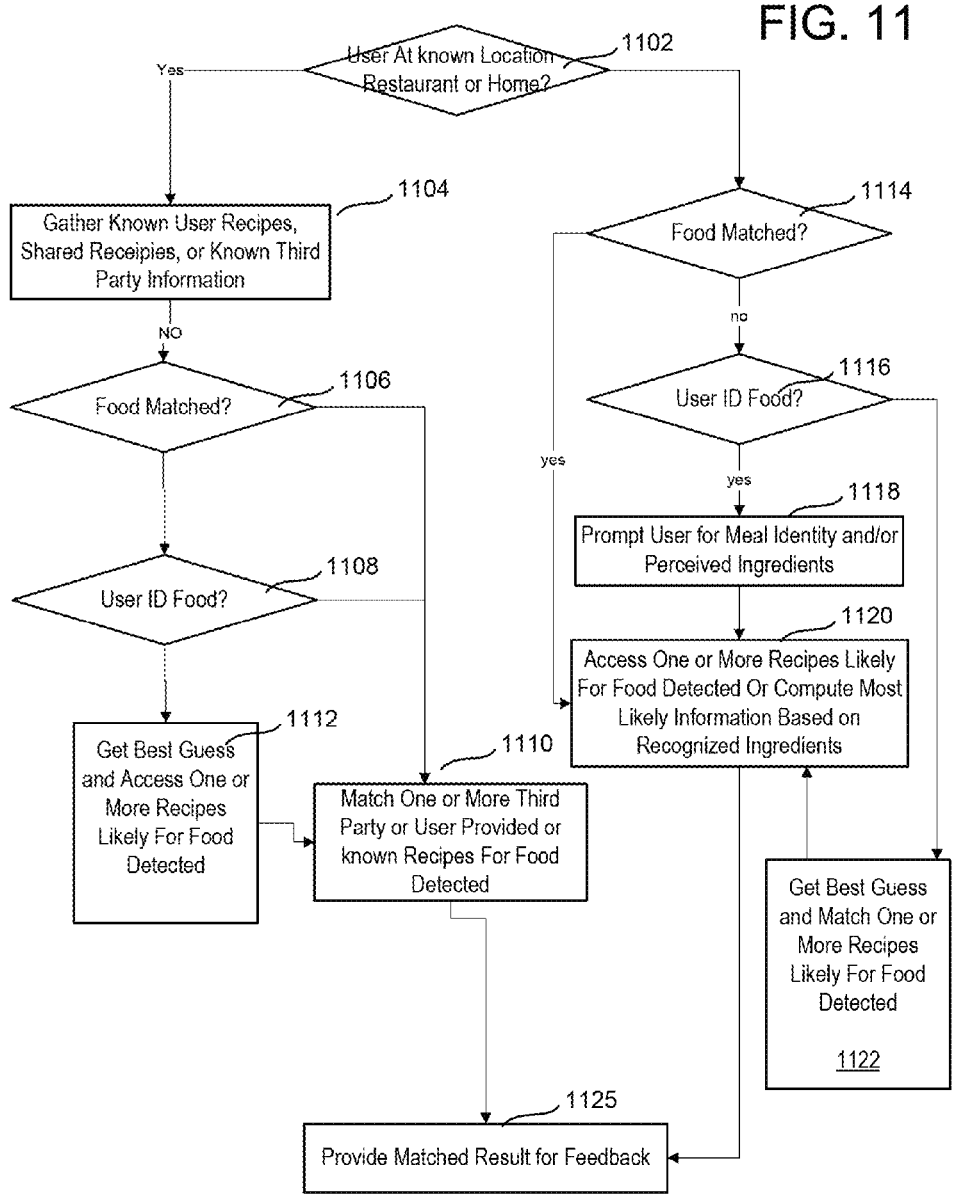

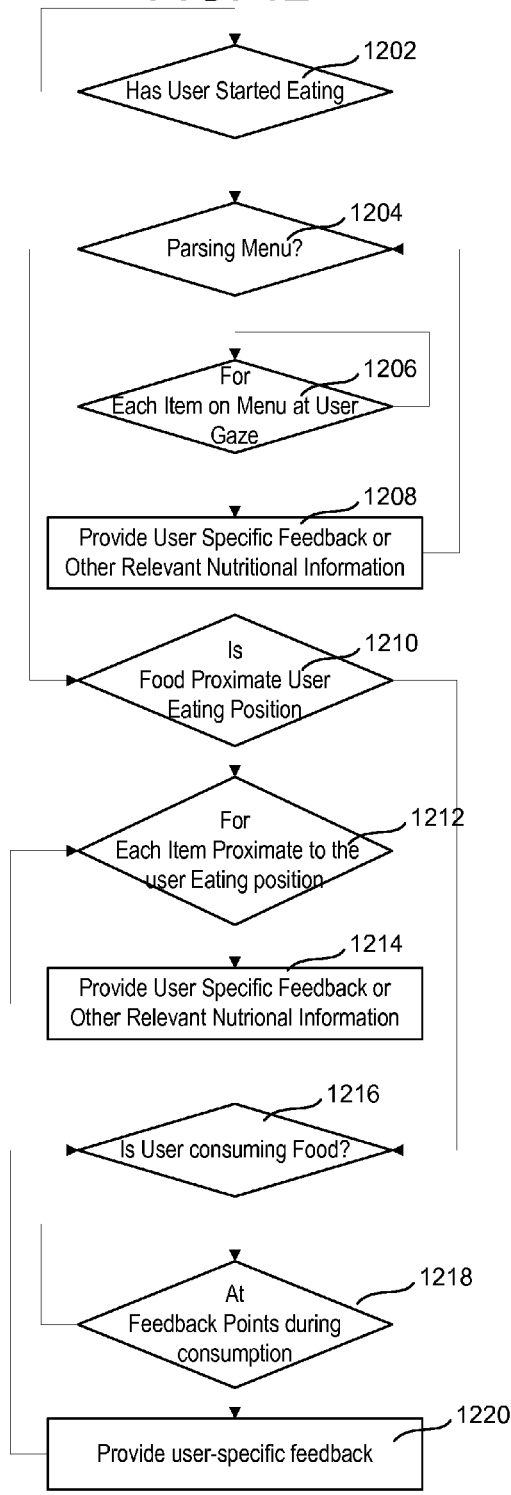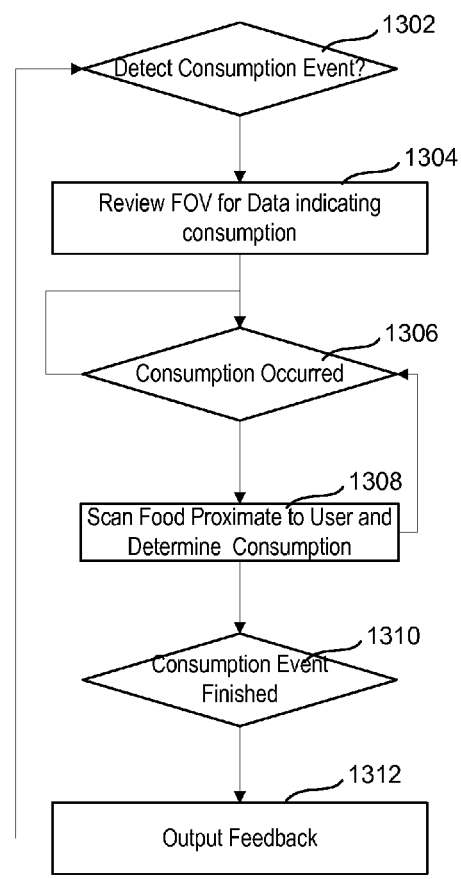

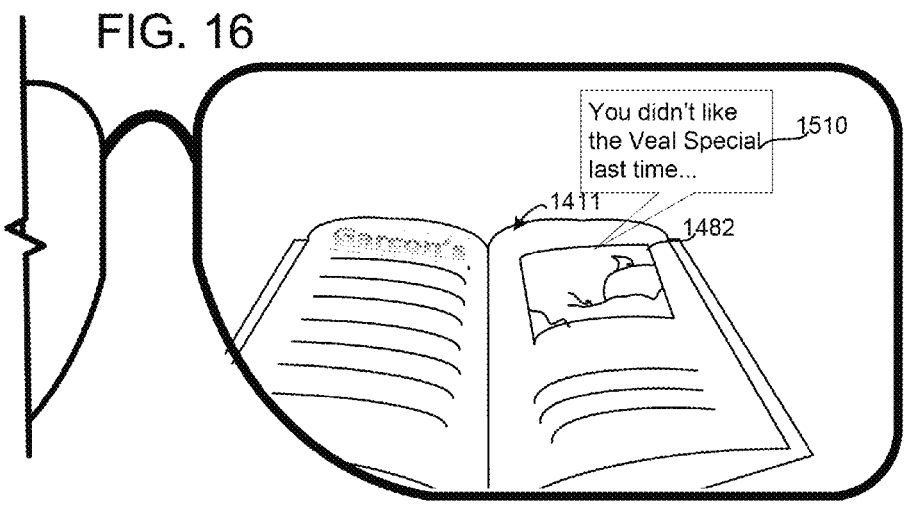
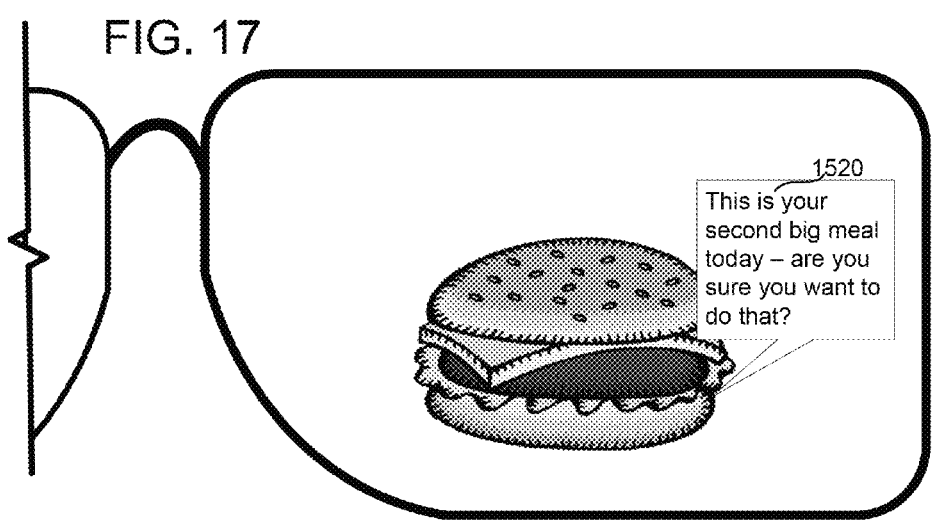

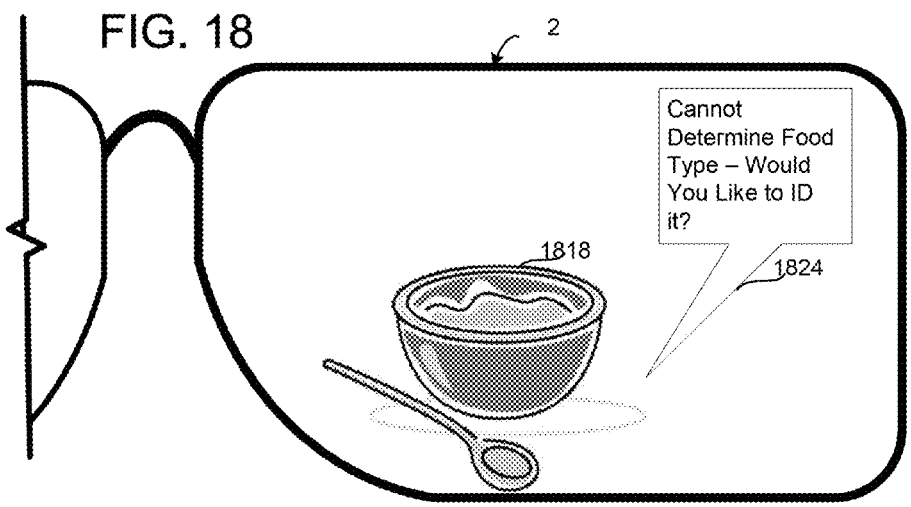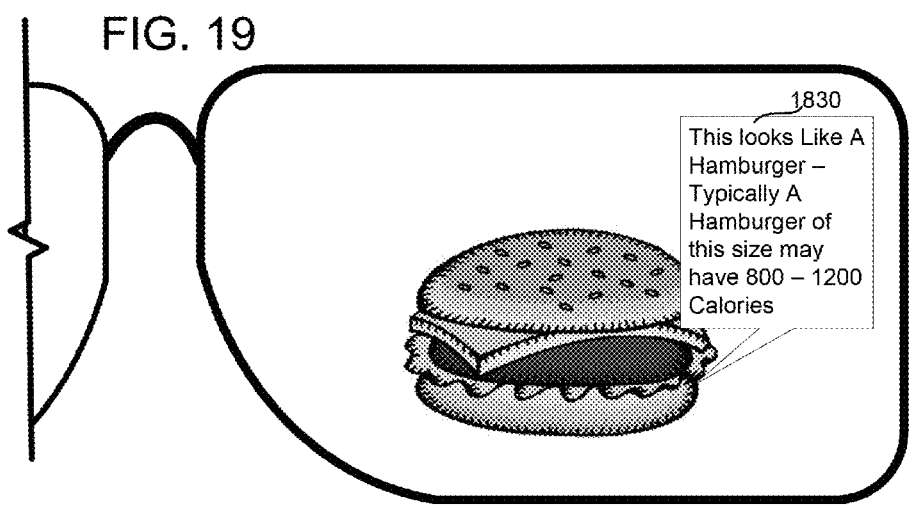

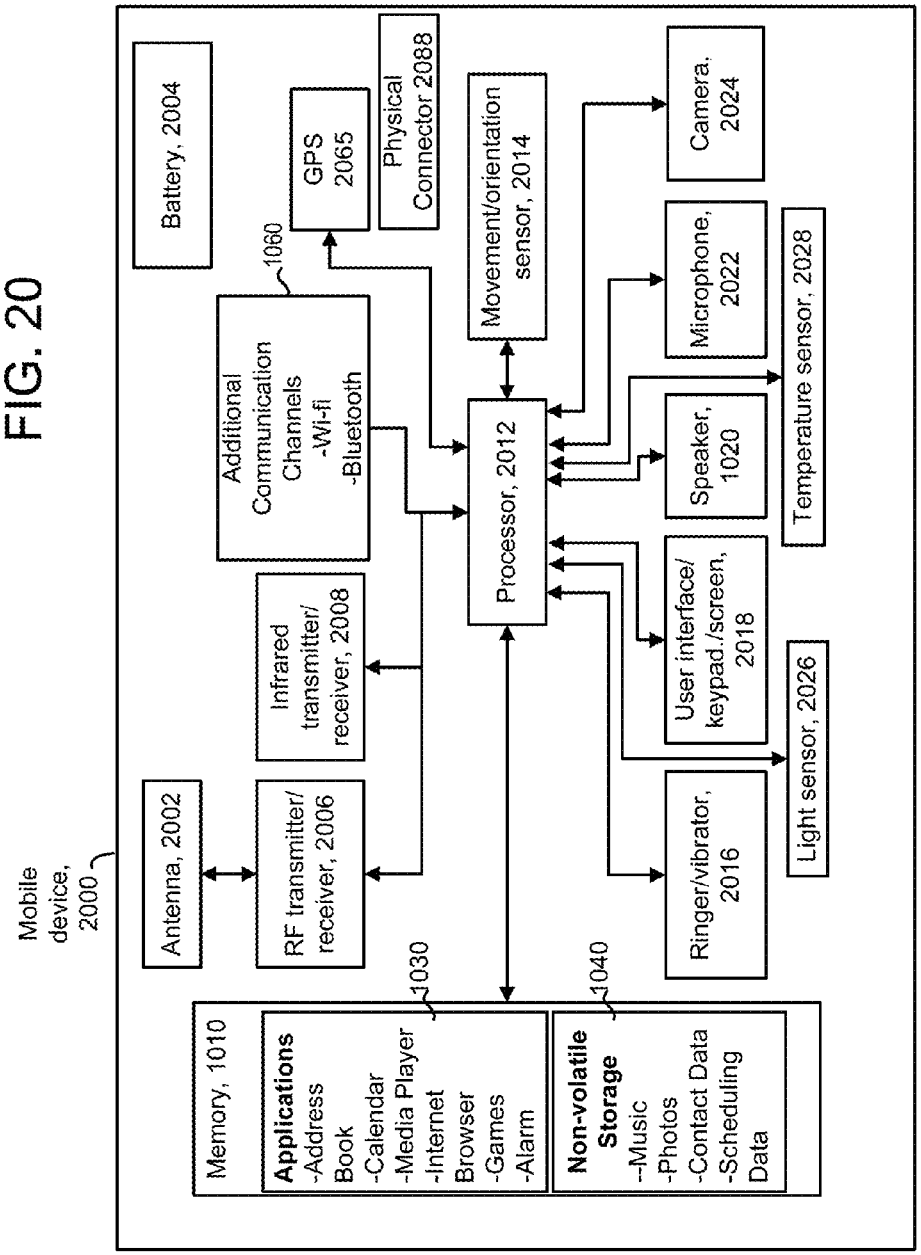

WEARABLE FOOD NUTRITION FEEDBACK SYSTEM

BACKGROUND

People are generally not aware of the nutritional information on food items they consume. While people may have general knowledge of the food items, calorie content, ingredients, and the benefits and consequences of the food they are presented with, tracking consumption and nutritional information for each meal is tedious. Providing nutritional information is advantageous for people trying to watch their weight, people with allergy restrictions, or strict dietary needs.

Mixed reality displays allow virtual imagery to be mixed with a real world physical environment in a display. Systems for mixed reality may include, for example, see through head mounted displays or smart phones with built in cameras that detect the area within a field of view of a wearer. Such systems typically include processing units which provide the imagery under the control of one or more applications.

SUMMARY

Technology is described to provide a wearable food nutrition feedback system. The feedback system includes a see-through, near-eye, head mounted display having a plurality of sensors detecting information in a field of view of the apparatus. Food items are detected in the field of view and various types of feedback are provided to the wearer of the device. Feedback can include warnings based on personal wearer needs, general nutrition information, food consumption tracking and social interactions. The system includes one or more processing devices in communication with display and the sensors which identify food items proximate to the apparatus, determine feedback information relevant to a wearer of the apparatus; and render feedback information in the display. The technology can be expanded for uses involving food preparation and shopping.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 3A is a flowchart of a method embodiment for aligning a see-through, near-eye, head mounted display with an IPD.

FIG. 3B is a flowchart of an implementation example of a method for adjusting a see-through, near-eye, head mounted display device for bringing the device into alignment with a wearer IPD.

FIG. 3C is a flowchart illustrating different example options of mechanical or automatic adjustment of at least one see-through, near-eye, head mounted display adjustment mechanism.

FIG. 4A is a side view of an eyeglass temple in an eyeglasses embodiment of a see-through, near-eye, head mounted display device providing support for hardware and software components.

FIG. 4B is a side view of an eyeglass temple in an embodiment of a see-through, near-eye, head mounted display device providing support for hardware and software components and three dimensional adjustment of a microdisplay assembly.

FIG. 5A is a top view of an embodiment of a movable display optical system of a see-through, near-eye, head mounted including an arrangement of gaze detection elements.

FIG. 5B is a top view of another embodiment of a movable display optical system of a see-through, near-eye, head mounted including an arrangement of gaze detection elements.

FIG. 5C is a top view of a third embodiment of a movable display optical system of a see-through, near-eye head mounted including an arrangement of gaze detection elements.

FIG. 5D is a top view of a fourth embodiment of a movable display optical system of a see-through, near-eye, head mounted including an arrangement of gaze detection elements.

FIG. 11 is a flowchart representing a method for determining nutritional information for food items available.

FIG. 12 is a flowchart representing a method for determining feedback for a wearer.

FIG. 13 is a flowchart illustrating a method for tracking food consumption

FIGS. 14-19 are perspective views illustrating various types of feedback provided to a wearer of a see-through, head mounted display device.

FIG. 20 is a block diagram of an exemplary processing device.

DETAILED DESCRIPTION

The technology described herein includes a see-through, head mounted display device providing a wearer with feedback regarding a wearer's interactions and consumption of food. Food items are detected in the field of view of the device and various types of feedback are provided to the wearer of the device. Feedback can include warnings based on personal wearer needs, general nutrition information, food consumption tracking and social interactions. The system identifies food items proximate to the wearer, determines feedback information relevant to a wearer of the apparatus, and renders feedback information in the display.

Third parties and user history is utilized to provide accurate and customized feedback for a wearer. Third party food providers can present specific nutritional information on products to a user. User health can be tracked, for both consumption and food interaction concerns, and warnings provided to a user when issues arise. The technology can be expanded for uses involving food preparation and shopping.

FIGS. 1-6 illustrate an exemplary see-through, display device suitable for implementing the system.

Figure 1A:
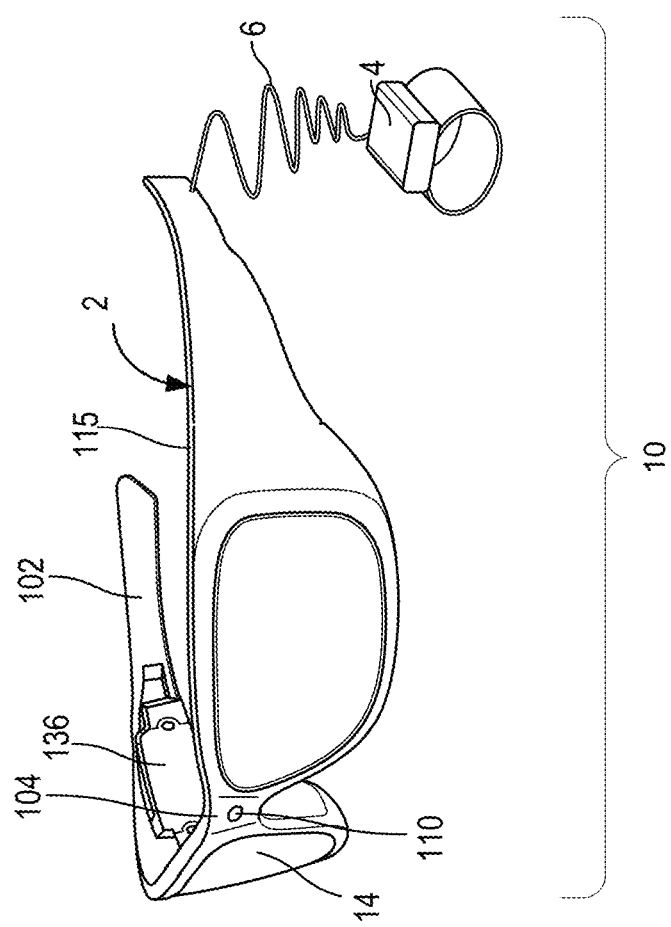
FIG. 1A is a block diagram depicting example components of one embodiment of a see-through, near-eye, head mounted device with adjustable IPD in a system environment in which the device may operate.

FIG. 1A is a block diagram depicting example components of one embodiment of a see-through, display device in a system environment in which the device may operate. In one embodiment, the technology implements a see through, near-eye display device. In other embodiments, see through display devices of different types may be used. System 10 includes a see-through display device as a near-eye, head mounted display device 2 in communication with processing unit 4 via wire 6. In other embodiments, head mounted display device 2 communicates with processing unit 4 via wireless communication. Processing unit 4 may take various embodiments. In some embodiments, processing unit 4 is a separate unit which may be worn on the wearer's body, e.g. the wrist in the illustrated example or in a pocket, and includes much of the computing power used to operate near-eye display device 2. Processing unit 4 may communicate wirelessly (e.g., WiFi, Bluetooth, infra-red, or other wireless communication means) to one or more computing systems, hot spots, cellular data networks, etc. In other embodiments, the functionality of the processing unit 4 may be integrated in software and hardware components of the display device 2.

See through head mounted display device 2, which in one embodiment is in the shape of eyeglasses in a frame 115, is worn on the head of a wearer so that the wearer can see through a display, embodied in this example as a display optical system 14 for each eye, and thereby have an actual direct view of the space in front of the wearer. The use of the term "actual direct view" refers to the ability to see real world objects directly with the human eye, rather than seeing created image representations of the objects. For example, looking through glass at a room allows a wearer to have an actual direct view of the room, while viewing a video of a room on a television is not an actual direct view of the room. Based on the context of executing software, for example, a gaming application, the system can project images of virtual objects, sometimes referred to as virtual images or holograms, on the display that are viewable by the person wearing the see-through display device while that person is also viewing real world objects through the display.

Frame 115 provides a support for holding elements of the system in place as well as a conduit for electrical connections. In this embodiment, frame 115 provides a convenient eyeglass frame as support for the elements of the system discussed further below. In other embodiments, other support structures can be used. An example of such a structure is a visor, hat, helmet or goggles. The frame 115 includes a temple or side arm for resting on each of a wearer's ears. Temple 102 is representative of an embodiment of the right temple and includes control circuitry 136 for the display device 2. Nose bridge 104 of the frame includes a microphone 110 for recording sounds and transmitting audio data to processing unit 4.

Figure 1B:
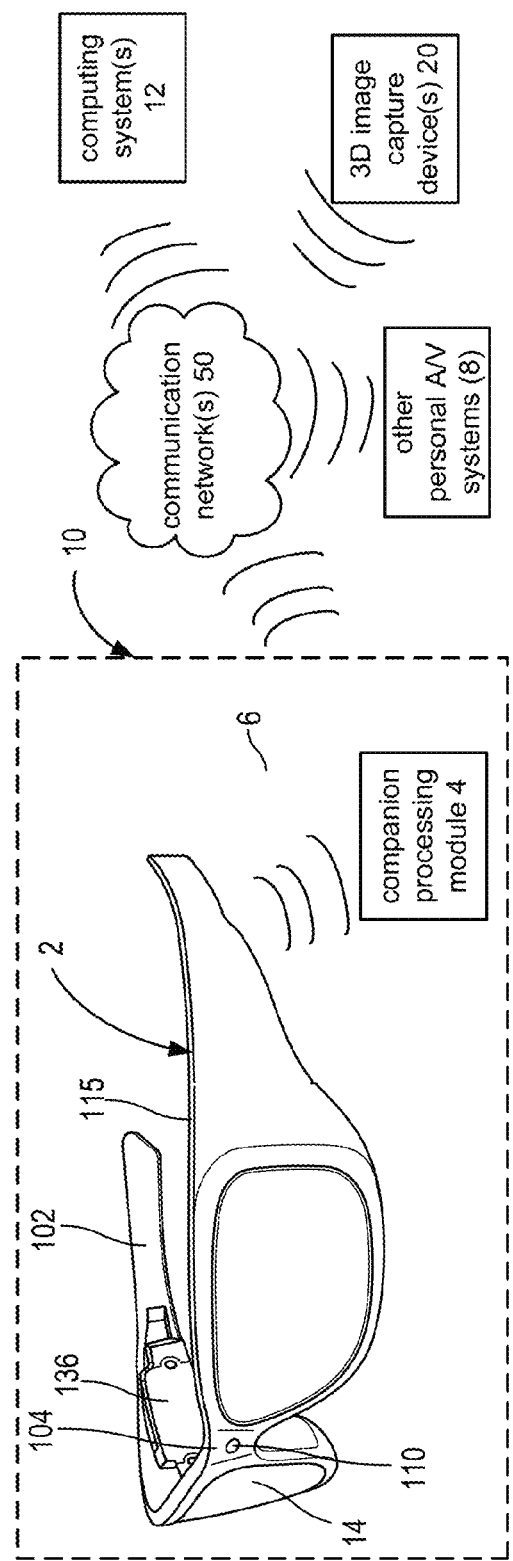
FIG. 1B is a block diagram depicting example components of another embodiment of a see-through, near-eye, head mounted device with adjustable IPD.

FIG. 1B is a block diagram depicting example components of another embodiment of a see-through, display device. In some embodiments, processing unit 4 is a separate unit which may be worn on the wearer's body, e.g. a wrist, or be a separate device like a mobile device (e.g. smartphone). The processing unit 4 may communicate wired or wirelessly (e.g., WiFi, Bluetooth, infrared, RFID transmission, wireless Universal Serial Bus (USB), cellular, 3G, 4G or other wireless communication means) over a communication network 50 to one or more computing systems 12 whether located nearby or at a remote location. In other embodiments, the functionality of the processing unit 4 may be integrated in software and hardware components of the display device 2.

One or more remote, network accessible computer system (s) 12 may be leveraged for processing power and remote data access. An example of hardware components of a computing system 12 is shown in FIG. 16. An application may be executing on computing system 12 which interacts with or performs processing for an application executing on one or more processors in the see-through, display system 10. For example, a 3D mapping application may be executing on the one or more computer systems 12 and the wearer's display system 10.

Additionally, in some embodiments, the applications executing on other see through head mounted display systems 10 in same environment or in communication with each other share data updates in real time, for example object identifications and occlusion data like an occlusion volume for a real object, in a peer-to-peer configuration between devices or to object management service executing in one or more network accessible computing systems.

The shared data in some examples may be referenced with respect to one or more referenced coordinate systems accessible to the device 2. In other examples, one head mounted display (HMD) device may receive data from another HMD device including image data or data derived from image data, position data for the sending HMD, e.g. GPS or IR data giving a relative position, and orientation data. An example of data shared between the HMDs is depth map data including image data and depth data captured by its front facing cameras 113, object identification data, and occlusion volumes for real objects in the depth map. The real objects may still be unidentified or have been recognized by software executing on the HMD device or a supporting computer system, e.g. 12 or another display system 10.

An example of an environment is a 360 degree visible portion of a real location in which the wearer is situated. A wearer may be looking at a subset of his environment which is his field of view. For example, a room is an environment. A person may be in a house and be in the kitchen looking at the top shelf of the refrigerator. The top shelf of the refrigerator is within his display field of view, the kitchen is his environment, but his upstairs bedroom is not part of his current environment as walls and a ceiling block his view of the upstairs bedroom. Of course, as he moves, his environment changes. Some other examples of an environment may be a ball field, a street location, a section of a store, a customer section of a coffee shop and the like. A location can include multiple environments, for example, the house may be a location. The wearer and his friends may be wearing their display device systems for playing a game which takes place throughout the house. As each player moves about the house, his environment changes. Similarly, a perimeter around several blocks may be a location and different intersections provide different environments to view as different cross streets come into view. In some instances, a location can also be an environment depending on the precision of location tracking sensors or data.

Figure 2A:
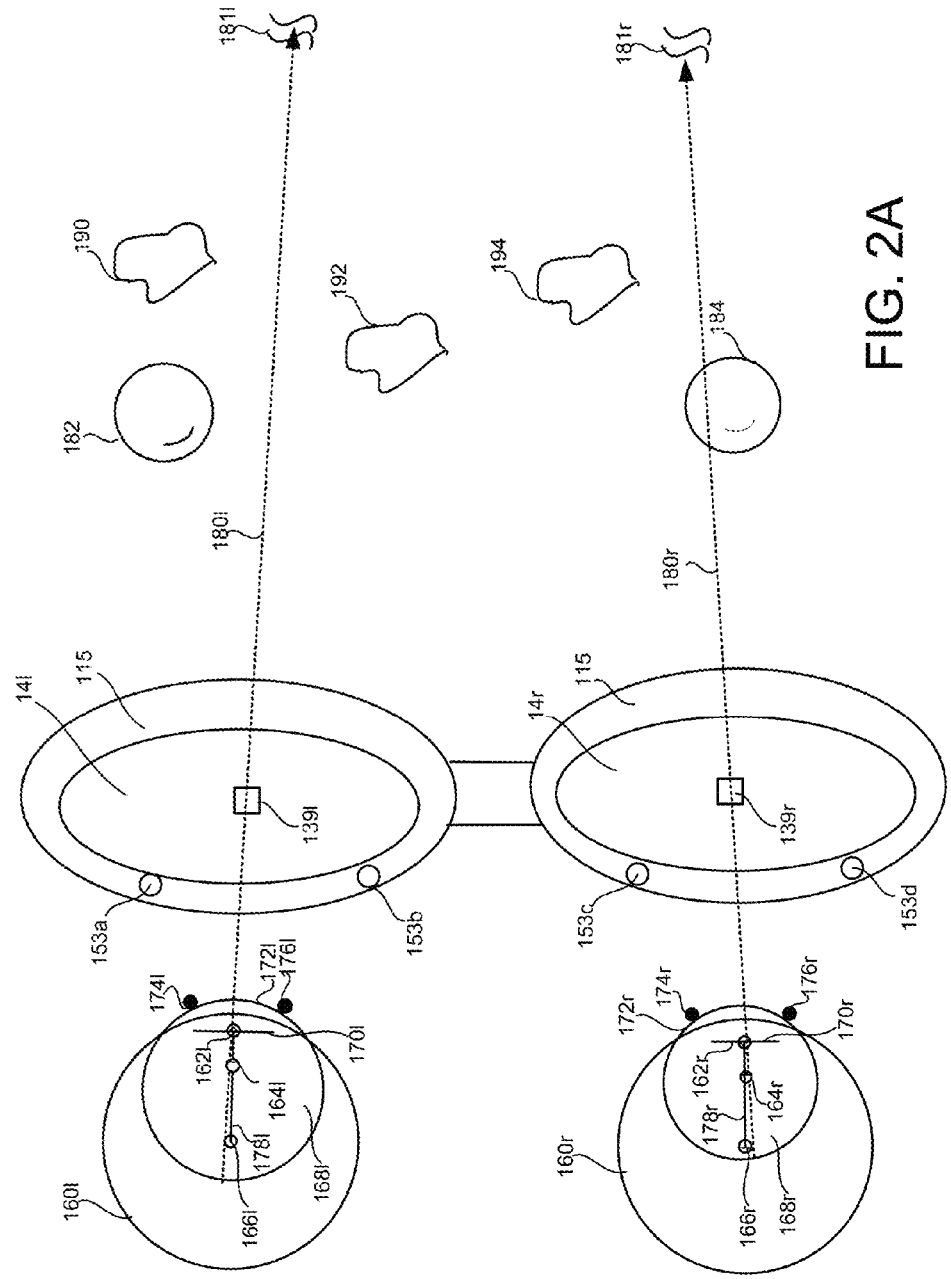
FIG. 2A is a top view illustrating examples of gaze vectors extending to a point of gaze at a distance and a direction for aligning a far IPD.

FIG. 2A is a top view illustrating examples of gaze vectors extending to a point of gaze at a distance and direction for aligning a far inter-pupillary distance (IPD). FIG. 2A illustrates examples of gaze vectors intersecting at a point of gaze where a wearer's eyes are focused effectively at infinity, for example beyond five (5) feet, or, in other words, examples of gaze vectors when the wearer is looking straight ahead. A model of the eyeball 160*l*, 160*r* is illustrated for each eye based on the Gullstrand schematic eye model. For each eye, an eyeball 160 is modeled as a sphere with a center 166 of rotation and includes a cornea 168 modeled as a sphere too and having a center 164. The cornea rotates with the eyeball, and the center 166 of rotation of the eyeball may be treated as a fixed point. The cornea covers an iris 170 with a pupil 162 at its center. In this example, on the surface 172 of the respective cornea are glints 174 and 176.

In the illustrated embodiment of FIG. 2A, a sensor detection area 139 (139*l* and 139*r*) is aligned with the optical axis of each display optical system 14 within an eyeglass frame 115. The sensor associated with the detection area is a camera in this example capable of capturing image data representing glints 174*l* and 176*l* generated respectively by illuminators 153*a* and 153*b* on the left side of the frame 115 and data representing glints 174*r* and 176*r* generated respectively by illuminators 153*c* and 153*d*. Through the display optical systems, 14*l* and 14*r* in the eyeglass frame 115, the wearer's field of view includes both real objects 190, 192 and 194 and virtual objects 182, 184, and 186.

The axis 178 formed from the center 166 of rotation through the cornea center 164 to the pupil 162 is the optical axis of the eye. A gaze vector 180 is sometimes referred to as the line of sight or visual axis which extends from the fovea through the center of the pupil 162. The fovea is a small area of about 1.2 degrees located in the retina. The angular offset between the optical axis computed and the visual axis has horizontal and vertical components. The horizontal component is up to 5 degrees from the optical axis, and the vertical component is between 2 and 3 degrees. In many embodiments, the optical axis is determined and a small correction is determined through wearer calibration to obtain the visual axis which is selected as the gaze vector.

For each wearer, a virtual object may be displayed by the display device at each of a number of predetermined positions at different horizontal and vertical positions. An optical axis may be computed for each eye during display of the object at each position, and a ray modeled as extending from the position into the wearer eye. A gaze offset angle with horizontal and vertical components may be determined based on how the optical axis is to be moved to align with the modeled ray. From the different positions, an average gaze offset angle with horizontal or vertical components can be selected as the small correction to be applied to each computed optical axis. In some embodiments, a horizontal component is used for the gaze offset angle correction.

The gaze vectors 180*l* and 180*r* are not perfectly parallel as the vectors become closer together as they extend from the eyeball into the field of view at a point of gaze which is effectively at infinity as indicated by the symbols 181*l* and 181*r*. At each display optical system 14, the gaze vector 180 appears to intersect the optical axis upon which the sensor detection area 139 is centered. In this configuration, the optical axes are aligned with the inter-pupillary distance (IPD). When a wearer is looking straight ahead, the IPD measured is also referred to as the far IPD.

When identifying an object for a wearer to focus on for aligning IPD at a distance, the object may be aligned in a direction along each optical axis of each display optical system. Initially, the alignment between the optical axis and wearer's pupil is not known. For a far IPD, the direction may be straight ahead through the optical axis. When aligning near IPD, the identified object may be in a direction through the optical axis, however due to vergence of the eyes at close distances, the direction is not straight ahead although it may be centered between the optical axes of the display optical systems.

Figure 2B:
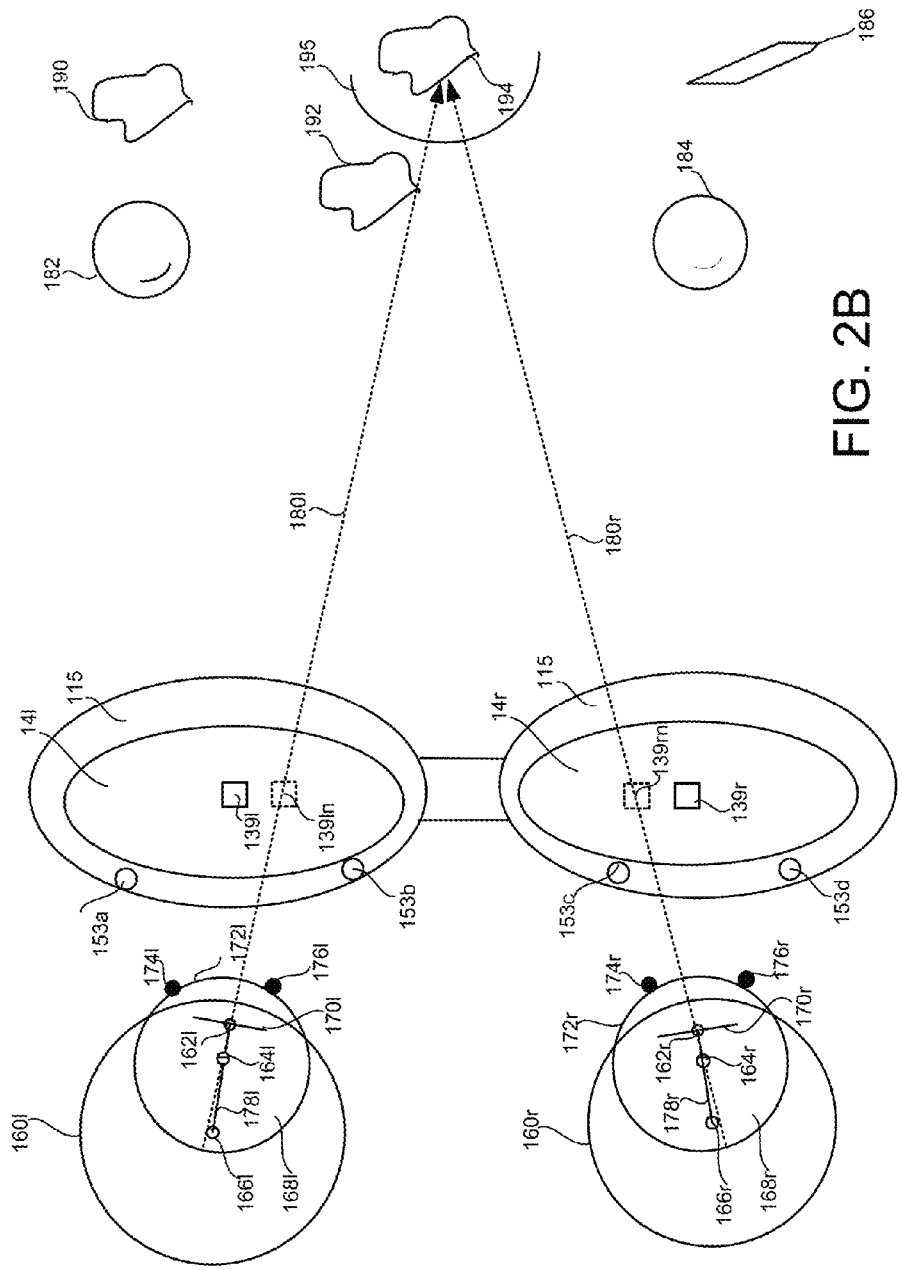
FIG. 2B is a top view illustrating examples of gaze vectors extending to a point of gaze at a distance and a direction for aligning a near IPD.

FIG. 2B is a top view illustrating examples of gaze vectors extending to a point of gaze at a distance and a direction for aligning a near IPD. In this example, the cornea 168*l* of the left eye is rotated to the right or towards the wearer's nose, and the cornea 168*r* of the right eye is rotated to the left or towards the wearer's nose. Both pupils are gazing at a real object 194 at a much closer distance, for example two (2) feet in front of the wearer. Gaze vectors 180*l* and 180*r* from each eye enter the Panum's fusional region 195 in which real object 194 is located. The Panum's fusional region is the area of single vision in a binocular viewing system like that of human vision. The intersection of the gaze vectors 180*l* and 180*r* indicates that the wearer is looking at real object 194. At such a distance, as the eyeballs rotate inward, the distance between their pupils decreases to a near IPD. The near IPD is typically about 4 mm less than the far IPD. A near IPD distance criteria, e.g. a point of gaze at less than four feet for example, may be used to switch or adjust the IPD alignment of the display optical systems 14 to that of the near IPD. For the near IPD, each display optical system 14 may be moved toward the wearer's nose so the optical axis, and detection area 139, moves toward the nose a few millimeters as represented by detection areas 139*ln* and 139*rn*.

Techniques for automatically determining a wearer's IPD and automatically adjusting the STHMD to set the IPD for optimal wearer viewing, are discussed in co-pending U.S. patent application Ser. No. 13/221,739 entitled Gaze Detection In A See-Through, Near-Eye, Mixed Reality Display; U.S. patent application Ser. No. 13/221,707 entitled Adjustment Of A Mixed Reality Display For Inter-Pupillary Distance Alignment; and U.S. patent application Ser. No. 13/221,662 entitled Aligning Inter-Pupillary Distance In A Near-Eye Display System, all of which are hereby incorporated specifically by reference.

In general, FIG. 3A shows is a flowchart of a method embodiment 300 for aligning a see-through, near-eye, display with an IPD. In step 301, one or more processors of the control circuitry 136, automatically determines whether a see-through, near-eye, display device is aligned with an IPD of a wearer in accordance with an alignment criteria. If not, in step 302, the one or more processors cause adjustment of the display device by at least one display adjustment mechanism for bringing the device into alignment with the wearer IPD. If it is determined the see-through, near-eye, display device is in alignment with a wearer IPD, optionally, in step 303 an IPD data set is stored for the wearer. In some embodiments, a display device 2 may automatically determine whether there is IPD alignment every time anyone puts on the display device 2. However, as IPD data is generally fixed for adults, due to the confines of the human skull, an IPD data set may be determined typically once and stored for each wearer. The stored IPD data set may at least be used as an initial setting for a display device with which to begin an IPD alignment check.

FIG. 3B is a flowchart of an implementation example of a method for adjusting a display device for bringing the device into alignment with a wearer IPD. In this method, at least one display adjustment mechanism adjusts the position of a at least one display optical system 14 which is misaligned. In step 407, one or more adjustment are automatically determined for the at least one display adjustment mechanism for satisfying the alignment criteria for at least one display optical system. In step 408, that at least one display optical system is adjusted based on the one or more adjustment values. The adjustment may be performed automatically under the control of a processor or mechanically as discussed further below.

FIG. 3C is a flowchart illustrating different example options of mechanical or automatic adjustment by the at least one display adjustment mechanism as may be used to implement step 408. Depending on the configuration of the display adjustment mechanism in the display device 2, from step 407 in which the one or more adjustment values were already determined, the display adjustment mechanism may either automatically, meaning under the control of a processor, adjust the at least one display adjustment mechanism in accordance with the one or more adjustment values in step 334. Alternatively, one or more processors associated with the system may electronically provide instructions as per step 333 for wearer application of the one or more adjustment values to the at least one display adjustment mechanism. There may be instances of a combination of automatic and mechanical adjustment under instructions.

Some examples of electronically provided instructions are instructions displayed by the microdisplay 120, the processing unit 4 or audio instructions through speakers 130 of the display device 2. There may be device configurations with an automatic adjustment and a mechanical mechanism depending on wearer preference or for allowing a wearer some additional control.

FIG. 4A illustrates an exemplary arrangement of a see through, near-eye, display device embodied as eyeglasses with movable display optical systems including gaze detection elements. What appears as a lens for each eye represents a display optical system 14 for each eye, e.g. 14r and 14l. A display optical system includes a see-through lens, e.g. 118 and 116 in FIGS. 5A-5b, as in an ordinary pair of glasses, but also contains optical elements (e.g. mirrors, filters) for seamlessly fusing virtual content with the actual direct real world view seen through the lenses 118, 116. A display optical system 14 has an optical axis which is generally in the center of the see-through lens 118, 116 in which light is generally collimated to provide a distortionless view. For example, when an eye care professional fits an ordinary pair of eyeglasses to a wearer's face, a goal is that the glasses sit on the wearer's nose at a position where each pupil is aligned with the center or optical axis of the respective lens resulting in generally collimated light reaching the wearer's eye for a clear or distortionless view.

In an exemplary display device 2, a detection area of at least one sensor is aligned with the optical axis of its respective display optical system so that the center of the detection area is capturing light along the optical axis. If the display optical system is aligned with the wearer's pupil, each detection area of the respective sensor is aligned with the wearer's pupil. Reflected light of the detection area is transferred via one or more optical elements to the actual image sensor of the camera in this example illustrated by dashed line as being inside the frame 115.

In one example, a visible light camera (also commonly referred to as an RGB camera) may be the sensor. An example of an optical element or light directing element is a visible light reflecting mirror which is partially transmissive and partially reflective. The visible light camera provides image data of the pupil of the wearer's eye, while IR photodetectors 152 capture glints which are reflections in the IR portion of the spectrum. If a visible light camera is used, reflections of virtual images may appear in the eye data captured by the camera. An image filtering technique may be used to remove the virtual image reflections if desired. An IR camera is not sensitive to the virtual image reflections on the eye.

In other examples, the at least one sensor is an IR camera or a position sensitive detector (PSD) to which the IR radiation may be directed. For example, a hot reflecting surface may transmit visible light but reflect IR radiation. The IR radiation reflected from the eye may be from incident radiation of illuminators, other IR illuminators (not shown) or from ambient IR radiation reflected off the eye. In some examples, sensor may be a combination of an RGB and an IR camera, and the light directing elements may include a visible light reflecting or diverting element and an IR radiation reflecting or diverting element. In some examples, a camera may be small, e.g. 2 millimeters (mm) by 2 mm.

Various types of gaze detection systems are suitable for use in the present system. In some embodiments which calculate a cornea center as part of determining a gaze vector, two glints, and therefore two illuminators will suffice. However, other embodiments may use additional glints in determining a pupil position and hence a gaze vector. As eye data representing the glints is repeatedly captured, for example at 30 frames a second or greater, data for one glint may be blocked by an eyelid or even an eyelash, but data may be gathered by a glint generated by another illuminator.

FIG. 4A is a side view of an eyeglass temple 102 of the frame 115 in an eyeglasses embodiment of a see-through, display device. At the front of frame 115 is physical environment facing video camera 113 that can capture video and still images. Particularly in some embodiments, physical environment facing camera 113 may be a depth camera as well as a visible light or RGB camera. For example, the depth camera may include an IR illuminator transmitter and a hot reflecting surface like a hot mirror in front of the visible image sensor which lets the visible light pass and directs reflected IR radiation within a wavelength range or about a predetermined wavelength transmitted by the illuminator to a CCD or other type of depth sensor. Other types of visible light camera (RGB camera) and depth cameras can be used. More information about depth cameras can be found in U.S. patent application Ser. No. 12/813,675, filed on Jun. 11, 2010, incorporated herein by reference in its entirety. The data from the sensors may be sent to a processor 210 of the control circuitry 136, or the processing unit 4 or both which may process them but which the unit 4 may also send to a computer system over a network or secondary computing system for processing. The processing identifies objects through image segmentation and edge detection techniques and maps depth to the objects in the wearer's real world field of view. Additionally, the physical environment facing camera 113 may also include a light meter for measuring ambient light.

Control circuitry 136 provides various electronics that support the other components of head mounted display device 2. More details of control circuitry 136 are provided below with respect to FIGS. 6A and 6B. Inside, or mounted to temple 102, are ear phones 130, inertial sensors 132, GPS transceiver 144 and temperature sensor 138. In one embodiment inertial sensors 132 include a three axis magnetometer 132A, three axis gyro 132B and three axis accelerometer 132C (See FIG. 7A). The inertial sensors are for sensing position, orientation, and sudden accelerations of head mounted display device 2. From these movements, head position may also be determined.

The display device 2 provides an image generation unit which can create one or more images including one or more virtual objects. In some embodiments a microdisplay may be used as the image generation unit. A microdisplay assembly 173 in this example comprises light processing elements and a variable focus adjuster 135. An example of a light processing element is a microdisplay 120. Other examples include one or more optical elements such as one or more lenses of a lens system 122 and one or more reflecting elements such as reflective elements 124a and 124b in FIGS. 6A and 6B or 124 in FIGS. 6C and 6D. Lens system 122 may comprise a single lens or a plurality of lenses.

Mounted to or inside temple 102, the microdisplay 120 includes an image source and generates an image of a virtual object. The microdisplay 120 is optically aligned with the lens system 122 and the reflecting element 124 or reflecting elements 124a and 124b as illustrated in the following Figures. The optical alignment may be along an optical path 133 including one or more optical axes. The microdisplay 120 projects the image of the virtual object through lens system 122, which may direct the image light, onto reflecting element 124 which directs the light into lightguide optical element 112 as in FIGS. 5C and 5D or onto reflecting element 124a (e.g. a mirror or other surface) which directs the light of the virtual image to a partially reflecting element 124b which combines the virtual image view along path 133 with the natural or actual direct view along the optical axis 142 as in FIGS. 5A-5D. The combinations of views are directed into a wearer's eye.

The variable focus adjuster 135 changes the displacement between one or more light processing elements in the optical path of the microdisplay assembly or an optical power of an element in the microdisplay assembly. The optical power of a lens is defined as the reciprocal of its focal length, e.g. 1/focal length, so a change in one effects the other. The change in focal length results in a change in the region of the field of view, e.g. a region at a certain distance, which is in focus for an image generated by the microdisplay assembly 173.

In one example of the microdisplay assembly 173 making displacement changes, the displacement changes are guided within an armature 137 supporting at least one light processing element such as the lens system 122 and the microdisplay 120 in this example. The armature 137 helps stabilize the alignment along the optical path 133 during physical movement of the elements to achieve a selected displacement or optical power. In some examples, the adjuster 135 may move one or more optical elements such as a lens in lens system 122 within the armature 137. In other examples, the armature may have grooves or space in the area around a light processing element so it slides over the element, for example, microdisplay 120, without moving the light processing element. Another element in the armature such as the lens system 122 is attached so that the system 122 or a lens within slides or moves with the moving armature 137. The displacement range is typically on the order of a few millimeters (mm). In one example, the range is 1-2 mm. In other examples, the armature 137 may provide support to the lens system 122 for focal adjustment techniques involving adjustment of other physical parameters than displacement. An example of such a parameter is polarization.

For more information on adjusting a focal distance of a microdisplay assembly, see U.S. Patent Publication No. 2012-0113092-A1, published on May 10, 2012, application Ser. No. 12/941,825, entitled "Automatic Variable Virtual Focus for Augmented Reality Displays," filed Nov. 8, 2010, having inventors Bar-Zeev et al. and which is hereby incorporated by reference.

In one example, the adjuster 135 may be an actuator such as a piezoelectric motor. Other technologies for the actuator may also be used and some examples of such technologies are a voice coil formed of a coil and a permanent magnet, a magnetostriction element, and an electrostriction element.

There are different image generation technologies that can be used to implement microdisplay 120. For example, microdisplay 120 can be implemented using a transmissive projection technology where the light source is modulated by optically active material, backlit with white light. These technologies are usually implemented using LCD type displays with powerful backlights and high optical energy densities. Microdisplay 120 can also be implemented using a reflective technology for which external light is reflected and modulated by an optically active material. The illumination is forward lit by either a white source or RGB source, depending on the technology. Digital light processing (DLP), liquid crystal on silicon (LCOS) and Mirasol® display technology from Qualcomm, Inc. are all examples of reflective technologies which are efficient as most energy is reflected away from the modulated structure and may be used in the system described herein. Additionally, microdisplay 120 can be implemented using an emissive technology where light is generated by the display. For example, a PicoP™ engine from Microvision, Inc. emits a laser signal with a micro mirror steering either onto a tiny screen that acts as a transmissive element or beamed directly into the eye (e.g., laser).

FIG. 4B is a side view of an eyeglass temple in another embodiment of a display device providing support for hardware and software components and three-dimensional adjustment of a microdisplay assembly. Some of the numerals illustrated in the FIG. 5A above have been removed to avoid clutter in the drawing. In embodiments where the display optical system 14 is moved in any of three dimensions, the optical elements represented by reflecting element 124 and the other elements of the microdisplay assembly 173, e.g. 120, 122 may also be moved for maintaining the optical path 133 of the light of a virtual image to the display optical system. An XYZ transport mechanism in this example made up of one or more motors represented by display adjustment mechanism 203 and shafts 205 under control of the processor 210 of control circuitry 136 (see FIG. 6A) control movement of the elements of the microdisplay assembly 173. An example of motors which may be used are piezoelectric motors. In the illustrated example, one motor is attached to the armature 137 and moves the variable focus adjuster 135 as well, and another display adjustment mechanism 203 controls the movement of the reflecting element 124.

FIG. 5A is a top view of an embodiment of a movable display optical system 14 of a see-through, near-eye, device 2 including an arrangement of gaze detection elements. A portion of the frame 115 of the near-eye display device 2 will surround a display optical system 14 and provides support for elements of an embodiment of a microdisplay assembly 173 including microdisplay 120 and its accompanying elements as illustrated. In order to show the components of the display system 14, in this case display optical system 14r for the right eye system, a top portion of the frame 115 surrounding the display optical system is not depicted. Additionally, the microphone 110 in bridge 104 is not shown in this view to focus attention on the operation of the display adjustment mechanism 203. As in the example of FIG. 4C, the display optical system 14 in this embodiment is moved by moving an inner frame 117r, which in this example surrounds the microdisplay assembly 173 as well. The display adjustment mechanism 203 is embodied in this embodiment provided as three axis motors which attach their shafts 205 to inner frame 117r to translate the display optical system 14, which in this embodiment includes the microdisplay assembly 173, in any of three dimensions as denoted by symbol 145 indicating three (3) axes of movement.

The display optical system 14 in this embodiment has an optical axis 142 and includes a see-through lens 118 allowing the wearer an actual direct view of the real world. In this example, the see-through lens 118 is a standard lens used in eye glasses and can be made to any prescription (including no prescription). In another embodiment, see-through lens 118 can be replaced by a variable prescription lens. In some embodiments, see-through, near-eye, head mounted display device 2 will include additional lenses.

The display optical system 14 further comprises reflecting reflective elements 124a and 124b. In this embodiment, light from the microdisplay 120 is directed along optical path 133 via a reflecting element 124a to a partially reflective element 124b embedded in lens 118 which combines the virtual object image view traveling along optical path 133 with the natural or actual direct view along the optical axis 142 so that the combined views are directed into a wearer's eye, right one in this example, at the optical axis, the position with the most collimated light for a clearest view.

A detection area of a light sensor is also part of the display optical system 14r. An optical element 125 embodies the detection area by capturing reflected light from the wearer's eye received along the optical axis 142 and directs the captured light to the sensor 134r, in this example positioned in the lens 118 within the inner frame 117r. As shown, the arrangement allows the detection area 139 of the sensor 134r to have its center aligned with the center of the display optical system 14. For example, if sensor 134r is an image sensor, sensor 134r captures the detection area 139, so an image captured at the image sensor is centered on the optical axis because the detection area 139 is. In one example, sensor 134r is a visible light camera or a combination of RGB/IR camera, and the optical element 125 includes an optical element which reflects visible light reflected from the wearer's eye, for example a partially reflective mirror.

In other embodiments, the sensor 134r is an IR sensitive device such as an IR camera, and the element 125 includes a hot reflecting surface which lets visible light pass through it and reflects IR radiation to the sensor 134r. An IR camera may capture not only glints, but also an infra-red or near infra-red image of the wearer's eye including the pupil.

In other embodiments, the IR sensor 134r is a position sensitive device (PSD), sometimes referred to as an optical position sensor. The depiction of the light directing elements, in this case reflecting elements, 125, 124, 124a and 124b in FIGS. 5A-5D are representative of their functions. The elements may take any number of forms and be implemented with one or more optical components in one or more arrangements for directing light to its intended destination such as a camera sensor or a wearer's eye.

Figure 6A:
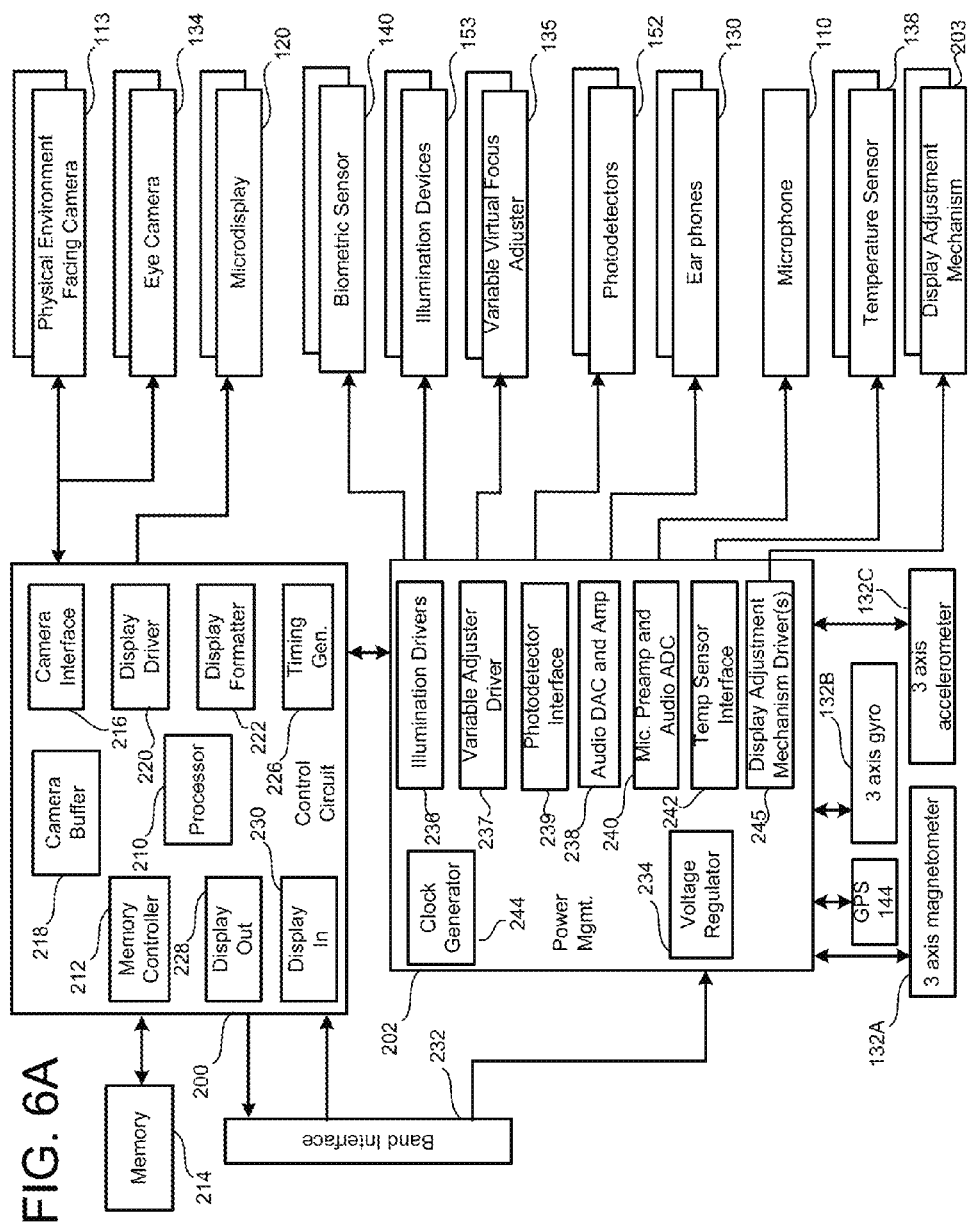
FIG. 6A is a block diagram of one embodiment of hardware and software components of a see-through, near-eye, head mounted display unit as may be used with one or more embodiments.

As discussed in FIGS. 2A and 2B above and in the Figures below, when the wearer is looking straight ahead, and the center of the wearer's pupil is centered in an image captured of the wearer's eye when a detection area 139 or an image sensor 134r is effectively centered on the optical axis of the display, the display optical system 14r is aligned with the pupil. When both display optical systems 14 are aligned with their respective pupils, the distance between the optical centers matches or is aligned with the wearer's inter-pupillary distance. In the example of FIG. 6A, the inter-pupillary distance can be aligned with the display optical systems 14 in three dimensions.

In one embodiment, if the data captured by the sensor 134 indicates the pupil is not aligned with the optical axis, one or more processors in the processing unit 4 or the control circuitry 136 or both use a mapping criteria which correlates a distance or length measurement unit to a pixel or other discrete unit or area of the image for determining how far off the center of the pupil is from the optical axis 142. Based on the distance determined, the one or more processors determine adjustments of how much distance and in which direction the display optical system 14r is to be moved to align the optical axis 142 with the pupil. Control signals are applied by one or more display adjustment mechanism drivers 245 to each of the components, e.g. display adjustment mechanism 203, making up one or more display adjustment mechanisms 203. In the case of motors in this example, the motors move their shafts 205 to move the inner frame 117r in at least one direction indicated by the control signals. On the temple side of the inner frame 117r are flexible sections 215a, 215b of the frame 115 which are attached to the inner frame 117r at one end and slide within grooves 217a and 217b within the interior of the temple frame 115 to anchor the inner frame 117 to the frame 115 as the display optical system 14 is move in any of three directions for width, height or depth changes with respect to the respective pupil.

In addition to the sensor, the display optical system 14 includes other gaze detection elements. In this embodiment, attached to frame 117r on the sides of lens 118, are at least two (2) but may be more, infra-red (IR) illuminators 153 which direct narrow infra-red light beams within a particular wavelength range or about a predetermined wavelength at the wearer's eye to each generate a respective glint on a surface of the respective cornea. In other embodiments, the illuminators and any photodiodes may be on the lenses, for example at the corners or edges. In this embodiment, in addition to the at least 2 infra-red (IR) illuminators 153 are IR photodetectors 152. Each photodetector 152 is sensitive to IR radiation within the particular wavelength range of its corresponding IR illuminator 153 across the lens 118 and is positioned to detect a respective glint. As shown in FIGS. 4A-4C, the illuminator and photodetector are separated by a barrier 154 so that incident IR light from the illuminator 153 does not interfere with reflected IR light being received at the photodetector 152. In the case where the sensor 134 is an IR sensor, the photodetectors 152 may not be used or may be an additional glint data capture source. With a visible light camera, the photodetectors 152 capture light from glints and generate glint intensity values.

In FIGS. 5A-5D, the positions of the gaze detection elements, e.g. the detection area 139 and the illuminators 153 and photodetectors 152 are fixed with respect to the optical axis of the display optical system 14. These elements may move with the display optical system 14r, and hence its optical axis, on the inner frame, but their spatial relationship to the optical axis 142 does not change.

FIG. 5B is a top view of another embodiment of a movable display optical system of a see-through, near-eye, device including an arrangement of gaze detection elements. In this embodiment, light sensor 134r may be embodied as a visible light camera, sometimes referred to as an RGB camera, or it may be embodied as an IR camera or a camera capable of processing light in both the visible and IR ranges, e.g. a depth camera. In this example, the image sensor 134r is the detection area 139r. The image sensor 134 of the camera is located vertically on the optical axis 142 of the display optical system. In some examples, the camera may be located on frame 115 either above or below see-through lens 118 or embedded in the lens 118. In some embodiments, the illuminators 153 provide light for the camera, and in other embodiments the camera captures images with ambient lighting or light from its own light source. Image data captured may be used to determine alignment of the pupil with the optical axis. Gaze determination techniques based on image data, glint data or both may be used based on the geometry of the gaze detection elements.

In this example, the display adjustment mechanism 203 in bridge 104 moves the display optical system 14r in a horizontal direction with respect to the wearer's eye as indicated by directional symbol 145. The flexible frame portions 215a and 215b slide within grooves 217a and 217b as the system 14 is moved. In this example, reflecting element 124a of a microdisplay assembly 173 embodiment is stationery. As the IPD is typically determined once and stored, any adjustment of the focal length between the microdisplay 120 and the reflecting element 124a that may be done may be accomplished by the microdisplay assembly, for example via adjustment of the microdisplay elements within the armature 137.

FIG. 5C is a top view of a third embodiment of a movable display optical system of a see-through, near-eye, device including an arrangement of gaze detection elements. The display optical system 14 has a similar arrangement of gaze detection elements including IR illuminators 153 and photodetectors 152, and a light sensor 134r located on the frame 115 or lens 118 below or above optical axis 142. In this example, the display optical system 14 includes a light guide optical element 112 as the reflective element for directing the images into the wearer's eye and is situated between an additional see-through lens 116 and see-through lens 118. As reflecting element 124 is within the lightguide optical element and moves with the element 112, an embodiment of a microdisplay assembly 173 is attached on the temple 102 in this example to a display adjustment mechanism 203 for the display optical system 14 embodied as a set of three axis mechanism 203 with shafts 205 include at least one for moving the microdisplay assembly. One or more display adjustment mechanism 203 on the bridge 104 are representative of the other components of the display adjustment mechanism 203 which provides three axes of movement. In another embodiment, the display adjustment mechanism may operate to move the devices via their attached shafts 205 in the horizontal direction. The mechanism 203 for the microdisplay assembly 173 would also move it horizontally for maintaining alignment between the light coming out of the microdisplay 120 and the reflecting element 124. A processor 210 of the control circuitry (see FIG. 7A) coordinates their movement.

Lightguide optical element 112 transmits light from microdisplay 120 to the eye of the wearer wearing head mounted display device 2. Lightguide optical element 112 also allows light from in front of the head mounted display device 2 to be transmitted through lightguide optical element 112 to the wearer's eye thereby allowing the wearer to have an actual direct view of the space in front of head mounted display device 2 in addition to receiving a virtual image from microdisplay 120. Thus, the walls of lightguide optical element 112 are see-through. Lightguide optical element 112 includes a first reflecting element 124 (e.g., a mirror or other surface). Light from microdisplay 120 passes through lens system 122 and becomes incident on reflecting element 124. The reflecting element 124 reflects the incident light from the microdisplay 120 such that light is trapped inside a planar, substrate comprising lightguide optical element 112 by internal reflection.

After several reflections off the surfaces of the substrate, the trapped light waves reach an array of selectively reflecting surfaces 126. Note that only one of the five surfaces 126 to prevent over-crowding of the drawing. Reflecting surfaces 126 couple the light waves incident upon those reflecting surfaces out of the substrate into the eye of the wearer. More details of a lightguide optical element can be found in United States Patent Application Publication 2008/0285140, Ser. No. 12/214,366, published on Nov. 20, 2008, "Substrate-Guided Optical Devices" incorporated herein by reference in its entirety. In one embodiment, each eye will have its own lightguide optical element 112.

FIG. 5D is a top view of a fourth embodiment of a movable display optical system of a see-through, near-eye, device including an arrangement of gaze detection elements. This embodiment is similar to FIG. 5C's embodiment including a light guide optical element 112. However, the only light detectors are the IR photodetectors 152, so this embodiment relies on glint detection only for gaze detection as discussed in the examples below.

In the embodiments of FIGS. 5A-5D, the positions of the gaze detection elements, e.g. the detection area 139 and the illuminators 153 and photodetectors 152 are fixed with respect to each other. In these examples, they are also fixed in relation to the optical axis of the display optical system 14.

In the embodiments above, the specific number of lenses shown are just examples. Other numbers and configurations of lenses operating on the same principles may be used. Additionally, in the examples above, only the right side of the see-through, near-eye, head mounted display device 2 are shown. A full near-eye, display device would include as examples another set of lenses 116 and/or 118, another lightguide optical element 112 for the embodiments of FIGS. 5C and 5D, another microdisplay 120, another lens system 122, likely another environment facing camera 113, another eye tracking sensor 134 for the embodiments of FIGS. 6A to 6C, earphones 130, and a temperature sensor 138.

Figure 6B:
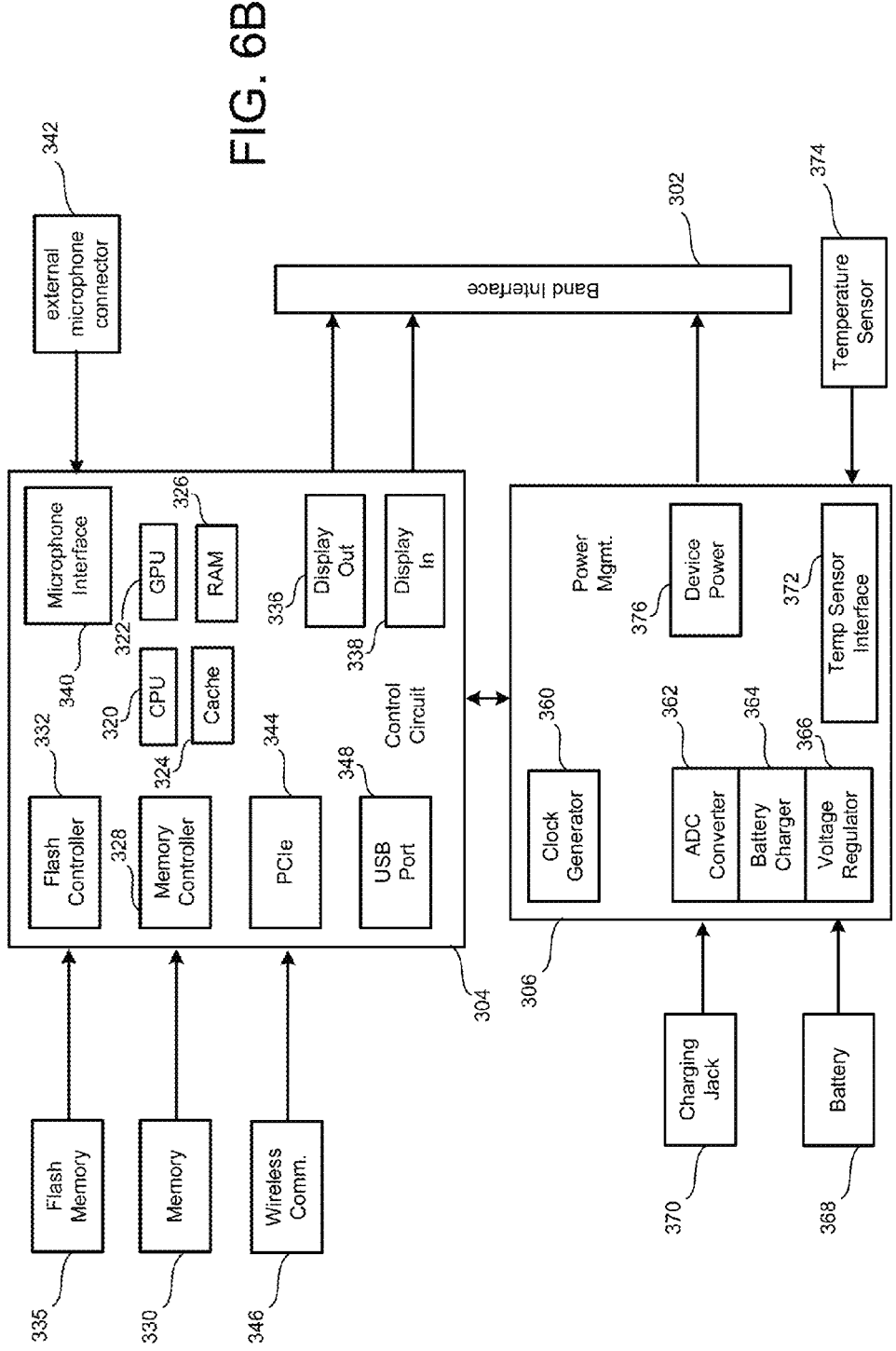
FIG. 6B is a block diagram of one embodiment of the hardware and software components of a processing unit associated with a see though, head mounted display device.

FIG. 6A is a block diagram of one embodiment of hardware and software components of a see-through, near-eye, display unit 2 as may be used with one or more embodiments. FIG. 7B is a block diagram describing the various components of a processing unit 4. In this embodiment, near-eye display device 2, receives instructions about a virtual image from processing unit 4 and provides the sensor information back to processing unit 4. Software and hardware components which may be embodied in a processing unit 4 are depicted in FIG. 6B, will receive the sensory information from the display device 2 (See FIG. 1A). Based on that information, processing unit 4 will determine where and when to provide a virtual image to the wearer and send instructions accordingly to the control circuitry 136 of the display device 2.

Note that some of the components of FIG. 6A (e.g., physical environment facing camera 113, eye sensor 134, variable virtual focus adjuster 135, detection area 139, microdisplay 120, illuminators 153, earphones 130, temperature sensor 138, display adjustment mechanism 203) are shown in shadow to indicate that there are at least two of each of those devices, at least one for the left side and at least one for the right side of head mounted display device 2. FIG. 6A shows the control circuit 200 in communication with the power management unit 202. Control circuit 200 includes processor 210, memory controller 212 in communication with memory 214 (e.g., D-RAM), camera interface 216, camera buffer 218, display driver 220, display formatter 222, timing generator 226, display out 228, and display in interface 230. In one embodiment, all of components of driver 220 are in communication with each other via dedicated lines of one or more buses. In another embodiment, each of the components of control circuit 200 are in communication with processor 210.

Camera interface 216 provides an interface to the two physical environment facing cameras 113 and each eye sensor 134 and stores respective images received from the cameras 113, sensor 134 in camera buffer 218. Display driver 220 will drive microdisplay 120. Display formatter 222 may provide information, about the virtual image being displayed on microdisplay 120 to one or more processors of one or more computer systems, e.g. 4, 210 performing processing for the augmented reality system. Timing generator 226 is used to provide timing data for the system. Display out 228 is a buffer for providing images from physical environment facing cameras 113 and the eye sensors 134 to the processing unit 4. Display in 230 is a buffer for receiving images such as a virtual image to be displayed on microdisplay 120. Display out 228 and display in 230 communicate with band interface 232 which is an interface to processing unit 4.

Power management unit 202 includes voltage regulator 234, eye tracking illumination driver 236, variable adjuster driver 237, photodetector interface 239, audio DAC and amplifier 238, microphone preamplifier and audio ADC 240, temperature sensor interface 242, display adjustment mechanism driver(s) 245 and clock generator 244. Voltage regulator 234 receives power from processing unit 4 via band interface 232 and provides that power to the other components of head mounted display device 2. Illumination driver 236 controls, for example via a drive current or voltage, the illuminators 153 to operate about a predetermined wavelength or within a wavelength range. Audio DAC and amplifier 238 receive the audio information from earphones 130. Microphone preamplifier and audio ADC 240 provide an interface for microphone 110. Temperature sensor interface 242 is an interface for temperature sensor 138. One or more display adjustment drivers 245 provide control signals to one or more motors or other devices making up each display adjustment mechanism 203 which represent adjustment amounts of movement in at least one of three directions. Power management unit 202 also provides power and receives data back from three axis magnetometer 132A, three axis gyro 132B and three axis accelerometer 132C. Power management unit 202 also provides power and receives data back from and sends data to GPS transceiver 144. In one embodiment, a biometric sensor 140 including for example a heartbeat sensor may be provided.

The variable adjuster driver 237 provides a control signal, for example a drive current or a drive voltage, to the adjuster 135 to move one or more elements of the microdisplay assembly 173 to achieve a displacement for a focal region calculated by software executing in a processor 210 of the control circuitry 13, or the processing unit 4, or both. In embodiments of sweeping through a range of displacements and, hence, a range of focal regions, the variable adjuster driver 237 receives timing signals from the timing generator 226, or alternatively, the clock generator 244 to operate at a programmed rate or frequency.

The photodetector interface 239 performs any analog to digital conversion needed for voltage or current readings from each photodetector, stores the readings in a processor readable format in memory via the memory controller 212, and monitors the operation parameters of the photodetectors 152 such as temperature and wavelength accuracy.

FIG. 6B is a block diagram of one embodiment of the hardware and software components of a processing unit 4 associated with a see-through, near-eye, display unit. The processing unit 4 may include this embodiment of hardware and software components as well as similar components which perform similar functions. FIG. 6B shows controls circuit 304 in communication with power management circuit 306. Control circuit 304 includes a central processing unit (CPU) 320, graphics processing unit (GPU) 322, cache 324, RAM 326, memory control 328 in communication with memory 330 (e.g., D-RAM), flash memory controller 332 in communication with flash memory 335 (or other type of non-volatile storage), display out buffer 336 in communication with see-through, near-eye, head mounted display device 2 via band interface 302 and band interface 232, display in buffer 338 in communication with near-eye display device 2 via band interface 302 and band interface 232, microphone interface 340 in communication with an external microphone connector 342 for connecting to a microphone, PCI express interface for connecting to a wireless communication component 346, and USB port(s) 348.

In one embodiment, wireless communication component 346 can include a Wi-Fi enabled communication device, Bluetooth communication device, infrared communication device, etc. The USB port can be used to dock the processing unit 4 to a secondary computing device in order to load data or software onto processing unit 4, as well as charge processing unit 4. In one embodiment, CPU 320 and GPU 322 are the main workhorses for determining where, when and how to insert images into the view of the wearer.

Power management circuit 306 includes clock generator 360, analog to digital converter 362, battery charger 364, voltage regulator 366, see-through, near-eye, head mounted display power interface 376, and temperature sensor interface 372 in communication with temperature sensor 374 (located on the wrist band of processing unit 4). An alternating current to digital converter 362 is connected to a charging jack 370 for receiving an AC supply and creating a DC supply for the system. Voltage regulator 366 is in communication with battery 368 for supplying power to the system. Battery charger 364 is used to charge battery 368 (via voltage regulator 366) upon receiving power from charging jack 370. Device power interface 376 provides power to the display device 2.

The system described above can be used to add virtual images to a wearer's view such that the virtual images are mixed with real images that the wearer see. In one example, the virtual images are added in a manner such that they appear to be part of the original scene. Examples of adding the virtual images can be found U.S. patent application Ser. No. 13/112,919, entitled "Event Augmentation With Real-Time Information," filed on May 20, 2011; and U.S. Patent Publication No. 2012-0092328-A1, published on Apr. 19, 2012, application Ser. No. 12/905,952, entitled "Fusing Virtual Content Into Real Content," filed on Oct. 15, 2010; both applications are incorporated herein by reference in their entirety.

Using the above-described device 2, the present technology implements a system for providing a wearer of the device 2 with feedback regarding food items available to a wearer both prior, during and after consumption. Where a wearer encounters any situation involving food, the wearer may be provided with nutritional and/or social feedback.

The technology will be described below with reference to use in providing feedback to a wearer in a situation involving the consumption of food items. It should be understood that the technology finds equal applicability in the preparation of meals using food items and in shopping for food items.

Figure 7:
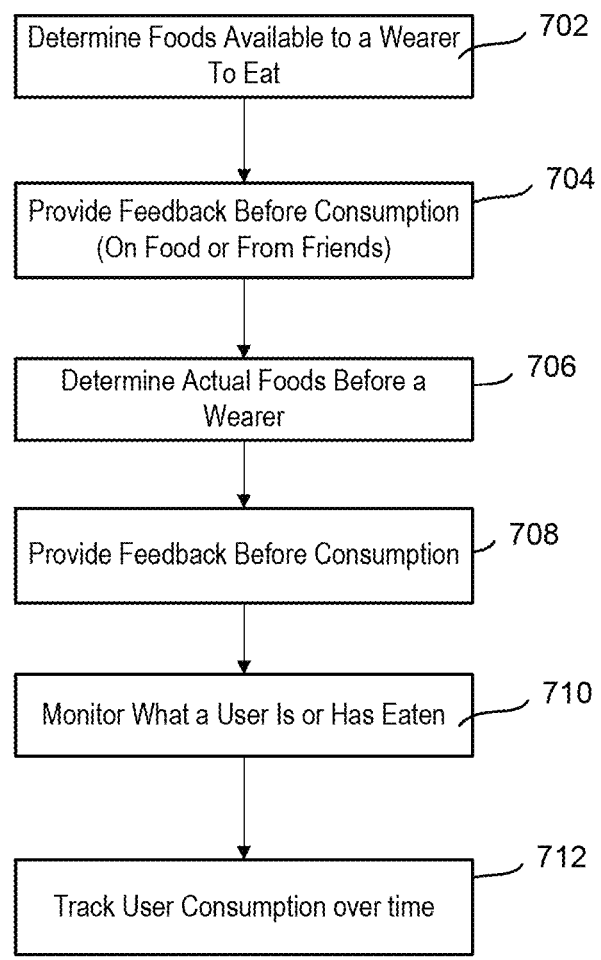
FIG. 7 is a flowchart representing a food feedback method in accordance with of the present technology.

FIG. 7 is a flowchart illustrating a general method in accordance with the present technology. At 702, a determination is made as to what food items are available to a wearer prior to the wearer being served to a wearer of a see-through head mounted display device 2. The determination of foods available to a wearer may be performed by any number of means, described below. The determination occurs, for example, when a wearer is at home and is about to prepare a meal. In this example, the wearer may have stocked their home with different types of food provided from a list available to the processing unit 4 or from items tracked by the device. The determination may occur, for example, if the wearer is known to be at a particular restaurant with a menu, accessing information for items on the menu, and identifying items based on wearer gaze at the menu. Alternatively, through the sensor data available from the device 2, food items can be identified by matching appearance with image and depth data associated with known food items. At 704, once the food has been determined, feedback can be provided to the wearer before consumption. The feedback may be in the form of nutritional information, specific wearer warnings based on wearer dietary concerns, or social information from friends. For example, if a wearer's friend has been at the particular location before, a recommendation can be shown showing the type of food that the wearer's friend ate and enjoyed. Similarly, if a wearer has an allergy to eating nuts, the system can provide warnings based on known or likely recipes which may contain nuts.

At 706, when food is presented to a wearer (and is proximate to the wearer), the system can determine which food items are currently before a wearer. While parsing a menu, a wearer may have a number of choices. In one example, it is possible to determine which item a wearer has chosen based on input via audio recognition from the microphone of system 2. Alternatively, when a plate is placed before the wearer and the food is proximate to the wearer, image data regarding the food can be used to determine the actual foods present before a wearer at 706.

At 708, feedback can be provided immediately before consumption of the meal. The feedback may be similar to the feedback provided at 704 or may be more specific, such as caloric information or warnings based on the wearer's dietary concerns. At 710, the technology can then monitor what a wearer or has eaten as the wearer consumes food proximate to the wearer. At 712, wearer consumption can be tracked over the meal, the day, the month, or longer to provide wearer feedback on the types of foods and the wearer's nutritional information.

Figure 8:
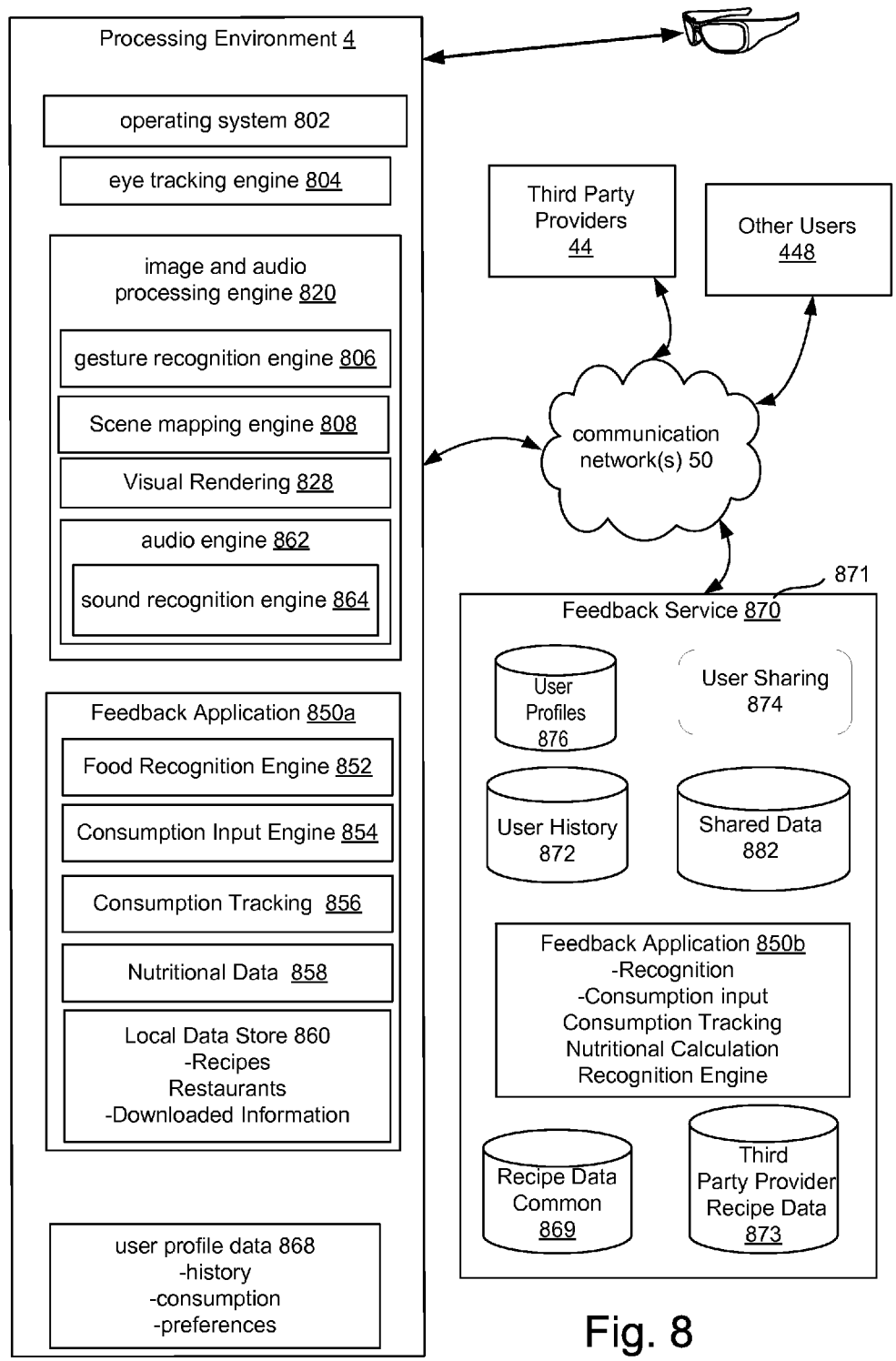
FIG. 8 is a block diagram representing a system for implementing the present technology.

FIG. 8 illustrates the functional components of a processing environment including the local processing unit 4 and a remote, network connected processing environment 871 implementing a feedback service 870. FIG. 8 is a block diagram of the system from a software perspective for providing a nutritional and food consumption feedback in a see-through head mounted display. FIG. 8 illustrates a computing environment which may be implemented by a personal computing apparatus in conjunction with one or more remote computing systems 870 in communication with the processing unit 4. Network connectivity via communication network 50 allows leveraging available computing resources on a remote system 870 to provide the feedback service.

As shown in the embodiment of FIG. 8, software components resident in a processing unit 4 comprise an operating system 802, an eye-tracking engine 804, an image and audio processing engine 820, a feedback application 850A, and a wearer profile data store 868. Operating system 802 provides the underlying structure to allow hardware elements in the processing unit 4 to interact with higher-level functions of the functional components shown in FIG. 8.

Eye tracking engine 804 tracks the wearer gaze with respect to movements of the eye relative to the device 2. Eye tracking engine 804 can identify the gaze direction and, in conjunction with image and audio processing engine 820, a point of gaze external to the wearer based on eye position, eye movements, and objects recognized the image and audio processing engine 820. Image and audio processing engine 820 receives sensor input data including video and image data, depth data, and audio data from one or more sensors described above provided on the device 2. Image and depth information may come from outward facing sensors captured as the wearer moves his or her head and body.

Image and audio processing engine 820 includes a gesture recognition engine 806, a visual rendering engine 828, an audio engine 862, and a sound recognition engine 864. Gesture recognition engine 806 identifies actions performed by a wearer indicating control, command, or other recognized movements to an executing application such as feedback application 850A. The action may be performed by a body part of a wearer, such as a hand or a finger, but may also include an eye blink sequence. In one embodiment, the gesture recognition engine 806 includes a collection of gesture filters, each comprising information concerning a gesture that may be performed by at least one part of a skeletal model. The gesture recognition engine 806 compares a skeletal model and movements associated with it derived from the captured image added to gesture filters and a gesture library to identify when a wearer has performed one or more gestures. In some examples, matching an image data to an food item data including, for example, an image model of a wearer's hand or finger during a gesture may be used rather than skeletal tracking for recognized gestures. Image and audio processing engine 820 processes image depth data and audio data received from one ore more capture devices which might be available at a given location.

Data for identification of food items from image data can be provided by scene mapping engine 808. 3D mapping of the display field of view of the display device 2 can be determined by the scene mapping engine 808, based on captured image data and depth data for the display field of view. A depth map can represent the captured image data and depth data. A view dependent coordinate system may be used for mapping of the display field of view as how a collision between object appears to a wearer depends on the wearer's point of view. An example of the view dependent coordinate system is an X, Y, Z, coordinate system in which the Z-axis or depth axis extends orthogonally or as a normal from the front of a see through display device 2. In some examples, the image and depth data for the depth map are presented in the display field of view is received from cameras 113 on the front of display device 2. The display field of view may be determined remotely or using a set of environment data which is previously provided based on a previous mapping using the scene mapping engine 808. Items identified by the scene mapping engine can be used by the feedback application 850a to determine food items in a display field of view.

Visual rendering engine 828 renders display elements in the wearer display, which can include instances of three-dimensional holographic virtual objects, two dimensional images, colors and other information within the display of a display device 2. Visual rendering engine 828 works in conjunction with application 850a to render elements in a display. An audio engine 862 interprets input from audio inputs such as microphone 110.

Feedback application 850A provides a wearer with food-related feedback before, during and after a wearer's interactions with food items. The feedback may be dietary, nutritional, personal and/or social. In some instances, the feedback can consider a wearer's location, third party information, and personal information, and provide the feedback within a wearer's field of view in a device 2. Application 850A includes a food recognition engine 852, a consumption input determination engine 854, consumption tracking engine 856, nutritional data 858, and a local data store 860. Food recognition engine 852 includes both a text processing and parsing component, and an food item recognition component. The text-parsing component can parse image input data from device 2 to discern items written on, for example, a restaurant menu at a known location to determine items available to the wearer when a wearer is gazing at one or more items on a menu. As a wearer rests his gaze on a particular item, feedback can be provided once the device determines the item that the wearer is looking at. The food item recognition component evaluates image date to determine whether food items match known patterns for food items. Food recognition engine 852 can also match input data such as image and depth data to known profiles for different types of foods. Certain types of foods will be more recognizable than others. For example, a hamburger is generally more defined than a simple breast of chicken. Hamburgers have multiple components that identify them as a particular item. A simple breast of chicken can be prepared in many ways, but the texture on the chicken can provide some clues to the food recognition engine as to how the dish is performed. As will be generally understood, food generally comprises dishes made up of more than one ingredient. As will be described below, food may be identified by one of a number of methods, and the ingredients in specific dishes retrieved from data provided by third parties, such as restaurants or food manufacturers, a wearer's own personal store of recipe data, or from a data store of common recipe data provided by the feedback service 870.

Application 850A includes a consumption input engine 854. The consumption input engine determines when and how much food a wearer may be consuming. Actual consumption of food items by a wearer can be determined based on gestures, sounds, or other indicators which will trigger a consumption input event, telling the system that the wearer is currently eating and allowing the system to identify which foods the wearer is eating by reference to foods identified by the food recognition engine. The input engine 854 determines which events identify consumption, and when a wearer is actually ingesting food. A consumption-tracking engine 856 computes a relationship between consumption input, and recognized or identified food consumed by the recognition engine 852 to determine how much a wearer has consumed over the course of a particular period of time. The time period may vary in accordance with the goals of the application provider, or may be set by a wearer. The consumption-tracking engine 856 allows the wearer to determine, over the period of time, how much the wearer has consumed and can provide valuable feedback to the wearer of a device. Nutritional data 858 includes information such as the recipes described above, as well as commonly understood and well-known data for ingredients which make up recipes. Nutritional data 858 can be utilized to build recipes and determine likely nutritional values, even if a third party does not provide specific nutritional values. For example, if the food recognition engine determines that a hamburger is proximate to the wearer and that the wearer is now consuming the hamburger, the nutritional data may include data based on the individual components making up a hamburger, a known or common recipe, and a calculation of what the likely nutritional value and components of the hamburger are.

Local data store 860 includes wearer specific recipes, third party nutrition information, common recipes and ingredient nutrition information. The information available in store 860 may be a subset of a larger set of such information available from the feedback service 870. This information may include, as noted above, recipes provided by third parties for specific dishes on their menus. This information may also include, for example, recipes provided by manufacturers so that a wearer knows that if a recipe is created in accordance with manufacturer instructions, a nutritional value can be accurately calculated. Wearer personal recipes which a wearer may input via the device 2 or, for example, through a wearer interface provided by the processing environment or feedback service to another processing environment.

User profile data store 868 includes wearer consumption history, wearer preferences, such as medical information and liked and disliked dishes, and other information allowing the feedback application 850a to provide data to the wearer. Additional information in the user profile data may be stored with the feedback service 870, but storage in the user profile store 868 and in the local data store 860 allow the feedback application to more rapidly access the information and provide valuable feedback to the wearer of the device 2.

Feedback service 870 may be provided on a plurality of processing devices 871 under the control of an administrator. Service 870 may include a user communication and sharing component 874 allowing one or more devices 2 to connect to the service via network 50. Third party providers 44 and other users 448 of display devices 2 can contribute data to the feedback service. The wearer profile store 876 includes wearer profile data such as that stored in users profile data store 868, as well as profiles for other wearers 448. Sharing may be enabled via the user-sharing component 874 to allow various wearers to share information in a social sharing component. User history 872 can include wearer history for individual users which can be shared with other wearers. For example, if a wearer visits a particular restaurant and a social friend has also visited the restaurant, the wearer may be provided with access to that social friend's previous experiences at the restaurant, allowing the wearer to enjoy the same meal or avoid a particularly unpleasant dish. Shared data 882 may include specifically shared information provided by other users 448. This may include comments, highlights, and reviews which may be shared with other wearers of similar devices via the wearer sharing component 874. The sharing component allows wearers to create typical social network sharing with other wearers, including creating public and private stores of information available to other wearers of the feedback service 870. A service based feedback application 850A includes the components shown in application 850A but may be run as part of the computing service 870.

Also shown in feedback service 870 are common recipe data 869 and third party provider recipe data 873. Common recipe data can include nutritional values for various types of dishes. For example, if the food recognition engine 852 determines that the wearer is sitting in front of a plate of veal parmigiana, but no recipe data is available for the specific dish, then the common recipe data can provide a sample listing for a typical recipe of veal parmigiana, a range of nutritional information for a "typical" dish which is proximate to a wearer.

Third provider recipe data 873 is data which is specific to manufacturers, restaurateurs, and/or locations. If, for example, a restaurant chain wishes to submit its third party recipe data to the feedback service 870, a wearer visiting any of the restaurants would have access to that chain's information. Similarly, individual restaurants can be identified by location and provide specific third party recipe data to the feedback service 870.

Figure 9:
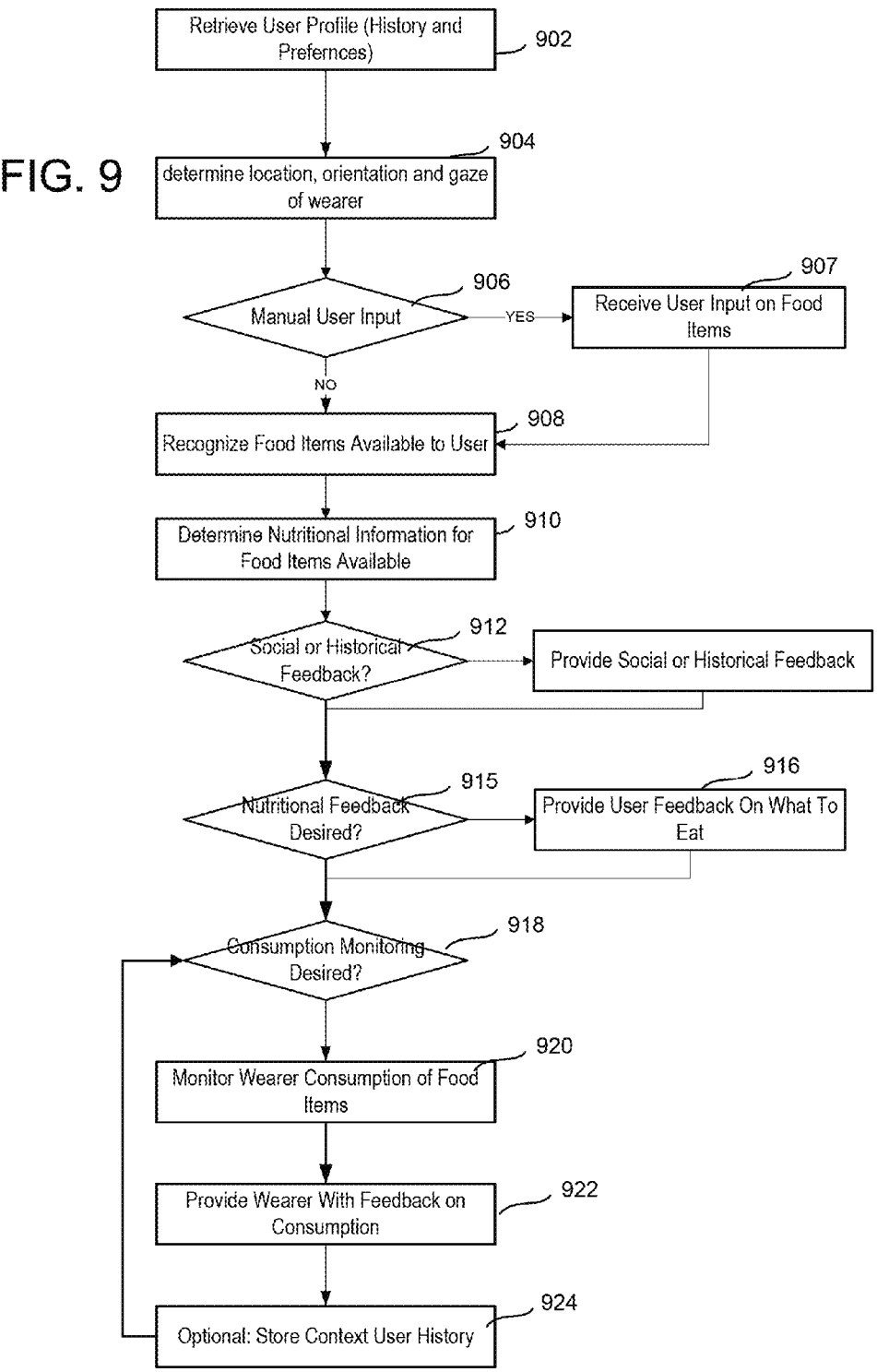
FIG. 9 is a second flowchart a food feedback method in accordance with the present technology.

FIG. 9 is a flowchart representing a more detailed method of a method for implementing the present technology. The method of FIG. 9 occurs when a wearer is about to consume food, such as when the wearer is visiting a restaurant and/or is about to begin a food consumption experience. At step 902, wearer profile is retrieved. In one embodiment, no wearer profile is used, and information is presented to a wearer without knowledge of wearer specific information. In the embodiment of FIG. 9, the wearer profile may include wearer consumption history, nutritional concerns, and wearer preferences. Preferences may include wearer typical likes and dislikes for types of dishes a wearer consumes, an indication of the type of feedback the wearer wishes to receive in the device, social friends, and other information to customize the feedback experience to a wearer of the device 2.

At step 904, the location orientation and gaze of the wearer is determined at 906. Location provides a reference for wearer and third party data which may be used to both identify food items and provide information on food items. Orientation and gaze may be used to determine what food items a wearer is interested in and may like feedback about. Determination of location orientation and gaze provides the system with an indication of whether the wearer may be at a restaurant, at home, or at some other location where the system can identify recipes from wearer data or third party data.

Steps 906 and 910 provide mechanisms for determining food items available to a wearer. Steps 906 and 908 may be provided in the sequence of FIG. 9, in a reversed order, or alone—each without the use of the other.

At 906, a wearer may be prompted to determine whether the wearer wishes to manually input the type of food which the wearer is about to consume. If a wearer does wish to input the type of food, the wearer can provide wearer input at 907. Wearer input can be provided by selecting from a menu of prepopulated choices driven by a wearer interface presented to the wearer in the device 2. The wearer interface can be derived from third party information based on the location of the wearer, or a menu driven by the food items recognized by the food recognition engine (e.g. by using the techniques described in FIG. 10 for step 908 below).

Once the wearer has input a food, or if the wearer does not wish to provide manual wearer input, a step 908, a determination is made as to what type of food is available and proximate to a wearer. Step 908 is detailed further below, but can comprise first determining, based on a location, whether third party or wearer specific data is available. For example, if the wearer is at home, wearer recipe data is likely to be useful in determining the type of food available. If the wearer is at a restaurant, the system can parse a menu available at the restaurant. Additional information on step 908 is discussed below with respect to FIG. 10.

Once the food items are recognized at 908, nutritional information is matched with the identified and available food items at 910.

Once the nutritional information for food items available has been determined at 912, the wearer may be prompted to ascertain what types of feedback the wearers wishes to see. It should be understood that the types of feedback might not be selectable as in FIG. 9. That is, the wearer may be provided with social and nutritional feedback without wearer input and solely as determined by the developer of application 850A.

At 912, a wearer may be prompted as to whether the wearer wishes his social or historical feedback. Social feedback can be provided in the form of recommendations from other wearers with whom the wearer of the device is a social media friend. If the wearer does wish to receive social feedback at 912, social feedback may be provided at 914 in accordance with the examples presented in FIG. 14-19. At 915, a wearer may decide whether or not the wearer wishes to receive nutritional feedback. If so, nutritional feedback of the detected food items can be presented to the wearer at 916. Examples of feedback presented to a wearer are shown in FIGS. 14-19.

Similarly, if consumption monitoring is desired at 918, then monitoring of wearer consumption takes place at 920 and feedback is provided at 922. Historical consumption feedback can be provided which indicates the number of meals a wearer has consumed to date, or a nutritional tally of how much the wearer has eaten over a specific period of time, such as a day, a week, or a month. Optionally, at step 924, wearer consumption history can be stored for later use in providing the wearer with feedback on their consumption.

Figure 10:
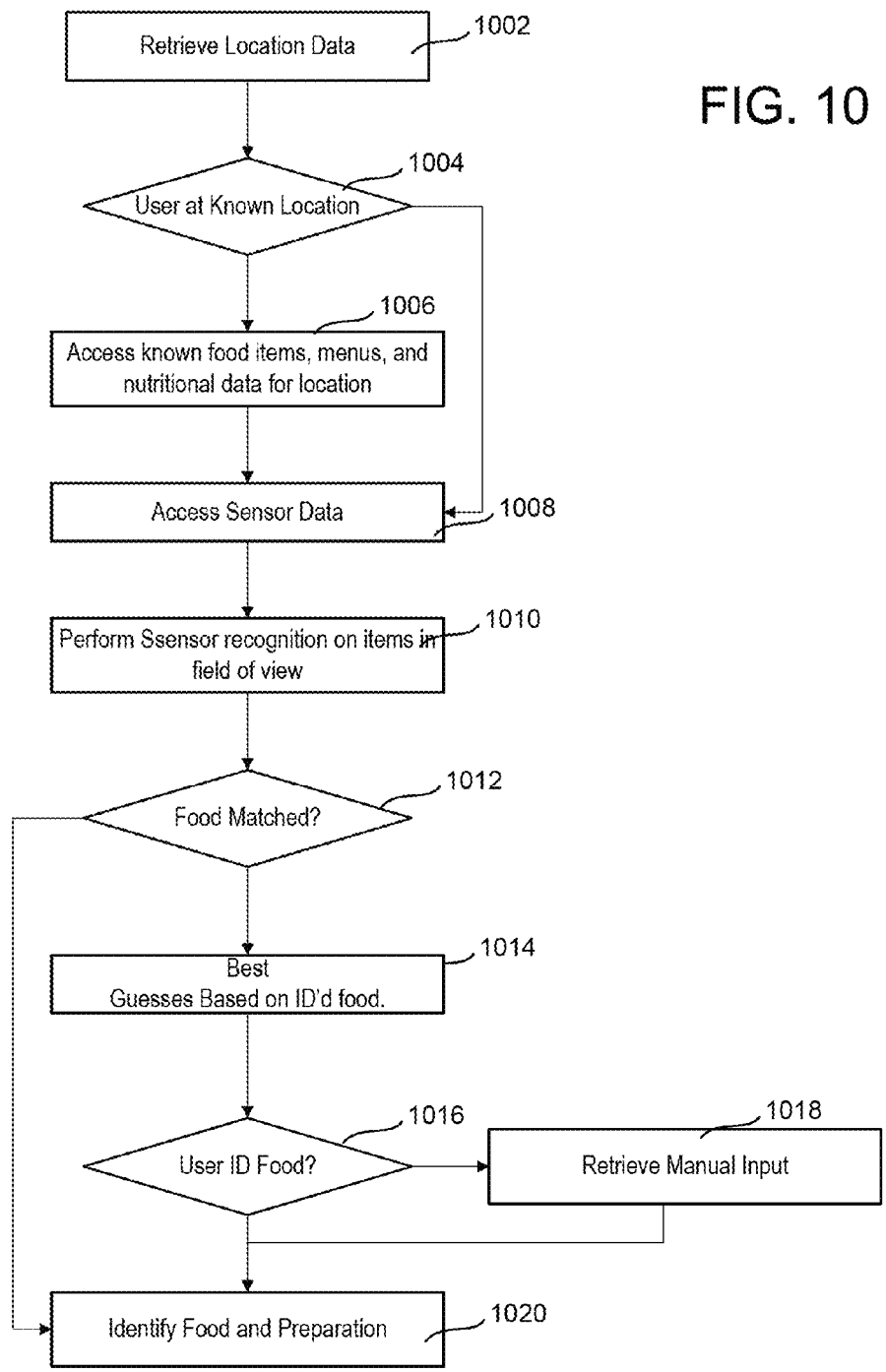
FIG. 10 is a flowchart representing a method for recognizing food items available to a wearer of a see-through, near-eye, head mounted display device.

FIG. 10 illustrates one exemplary method for performing step 908 of FIG. 9 of recognizing food items available to the wearer. At step 1002, location data is retrieved. As noted above, location data is useful in determining what items may be available to a user when a user is at a known location. In one alternative, location data is not utilized and third party data may be associated with the food items in a different manner, such as by QR codes or other scan tags. At step 1004, if the wearer is in a known location (or data is associable by other means) then at step 1006 data for known food items associated with the location or the identification event, such as menus, and nutritional data, is accessed. If the location is not known, or after accessing known data, sensor data from the device 2 is accessed at 1008. At 1010, sensor recognition is performed to determine whether food items available to the user can be ascertained. This includes performing one or all of image, text or other types of data recognition to identify items in the wearer field of view. Data for known food types—ingredients, recipes, and presentations—may be stored in local storage 860 and matched to sensor data at step 1012 to determine whether or not items within the wearer field of view are recognized. If items are recognized, the food and the type of preparation can be used for the nutritional information at 1020. If the food cannot be matched, a best guess may be made at step 1014. For example, where an imperfect matching occurs, an item which looks like a hamburger may also appear as a chicken sandwich, a turkey burger, or a vegetable burger. At step 1014, if a developer determined level of uncertainty in a match at 1012 occurs, then one or more alternatives may be provided at 1014. If the wearer is in an unknown location, and the system determines that an item which appears similar to a hamburger is within the field of view of a wearer and proximate to the wearer, the system may prompt the wearer with an indication that it thinks the item is a "hamburger," but could also be one of the chicken sandwich, vegetable burger, or turkey burger.

Where a low level of uncertainty in the match occurs, the user may be provided with an opportunity to identify the food item(s) at 1016. If the wearer chooses to select the item the wearer will provide manual input at 1018. If the wearer does not ID the foot, then the best guess is utilized at 1020.

FIG. 11 is a method for performing step 910 of FIG. 9 of determining the nutritional information for the food items available in the wearer field of view. Again, at step 1102, an initial determination is made as to whether or not the wearer is at a known location such as a restaurant or home. Again, other methods of associating data with the determination of nutritional information may be utilized. In this case, location or data association is used to access data on the nutritional information of identified food, rather than to identify the food items themselves.

If the wearer is at a known location (or information is otherwise associable with the event) then at 1104, known wearer recipes, shared recipes or third party recipes are retrieved. At 1106, if a food match has occurred (in step 1012, for example) then the one or more third provided or wearer provided recipes for the food detected is matched to the food item at 1110 and the data is provided for nutritional feedback at 1125. If the food is not matched at 1106, but the wearer IDs the food at 1108 (such as, for example, by step 1018), then the method again proceeds to step 1110. If the wearer has not ID'd the food and the food cannot be matched at 1106, then the best guess data is used at 1112 for the nutritional data. If the wearer is not at a known location (or no additional data is available) then if the food can be matched at 1114, then the method retrieves one or more recipes likely for the food detected based on the match, or computed the mote likely nutritional components available based on the recognized ingredients at 1120 and returns this data at 1125. If the food cannot be matched at, then a wearer is provided with an opportunity to identify the food at 1116 and if the wearer wishes to identify the food, then at 1118 the wearer can be prompted for prepared meals and/or perceived ingredients which the wearer can visibly ascertain. Once the wearer provides this information at 1118, the system can access one or more recipes likely for the food detected at 1120. If the wearer does not wish to ID the food and the food cannot be matched, then the system retrieves the best guess data based on the food recognition process of FIG. 10 and accesses one or more recipes likely for the food detected at 1120.

It should be recognized that in either FIG. 9 or FIG. 10, if best guess data is not available, the method might simply indicate to the user that the food items may not be identified.

FIG. 12 is a flowchart illustrating the method for providing wearer feedback on what to eat, which may be one method of performing step 916 in FIG. 9. At step 1202, the method begins when a wearer has started eating an eating event—when the user sits to eat or review a menu. Whether a using is eating can be determined by the gestures made by the wearer, sounds, and other actions within the field of view of the device 2. Once a wearer has started an eating event, at 1204 a determination is made as to whether or not a wearer is reviewing a menu. If the wearer is reviewing a menu, for each item that a wearer gazes at on the menu at 1206, specific wearer feedback or other relevant nutritional information can be provided at 1208. Once a wearer is done reviewing a menu, the system waits for food to be proximate to the wearer at 1210. In the context of this disclosure, food items proximate to the wearer are food items which are within the wearer's reach or field of view. For example, if a wearer's gaze rests on the food in front of him, at step 1212, a determination is made that an item is proximate to the wearer eating position and at 1214, specific feedback or other relevant nutritional information can be provided for the item where the wearer's gaze rests or pauses. Once a wearer begins consuming food at 1216, at random or predetermined feedback points 1218, feedback can be provided to the wearer at 1220. Feedback points can be determined by time, the rate of consumption of a wearer, the type of environment a wearer is in (a house or a restaurant) or other data specifically determined by the application provider.

FIG. 13 is a flowchart illustrating a method for monitoring a wearer's consumption of food at step 920 in FIG. 9. At step 1302, a consumption event is determined. A consumption event can be, for example, a gesture recognizing the wearer as bringing food to the wearer's mouth, a detection that the wearer is chewing food, or other sounds or gestures which indicate to the system that the wearer is actually consuming food. At 1304, the field of view is reviewed to determine whether there is data indicating consumption. For example, if a bite has been removed from hamburger which is proximate to a wearer, a determination can be made that the wearer is actually consuming the food, thereby verifying the consumption event at 1302. If consumption has in fact occurred at 1306, then the area proximate to the wearer can be scanned at 1308. A determination is made at 1310 as to whether or not the consumption event has finished. Once the consumption event is finished, feedback can be output at 1312. It should be understood that feedback can be output at any number of various times prior to the finishing of the consumption event.

FIGS. 14-19 illustrate various types of feedback described above which may be provided to a wearer. FIGS. 14-19 represent one side of a wearer's view in a display device 2 though, for example, lenses 118, 116. Although only one side of the display is illustrated, it will be understood that the display is equivalent in both lenses.

Figure 14:
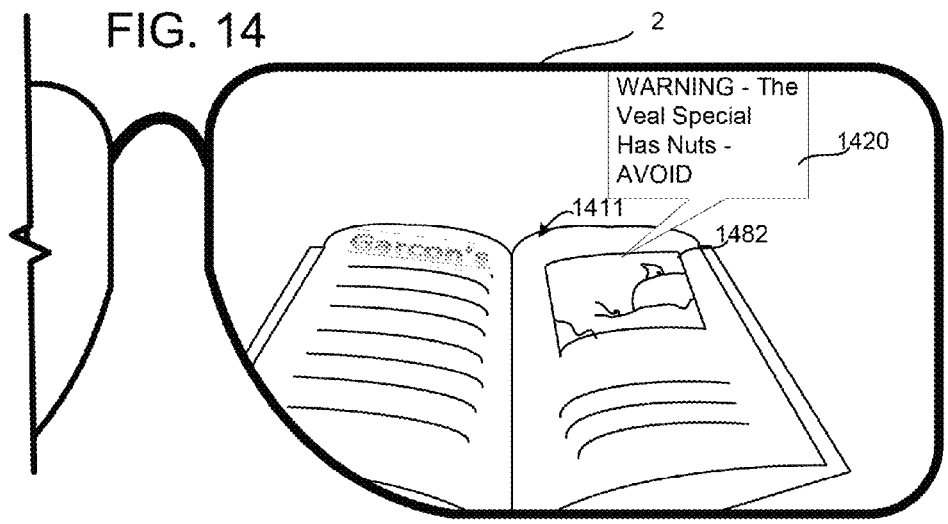

In FIG. 14, in the view of the wearer, a menu 1411 is shown having a menu item 1482. In the example shown in FIG. 14, a special item 1482 is recognized by the device 2. This may be performed by matching known restaurant data to a recognized menu item. A warning screen 1420 is shown indicating to the wearer that the wearer should not consume the "veal special" since the veal special is known to have nuts. The restaurant owner may provide the information on the preparation of the "veal special" in third party data, while the user concern for nuts may be recognized in the user profile data.

Figure 15:
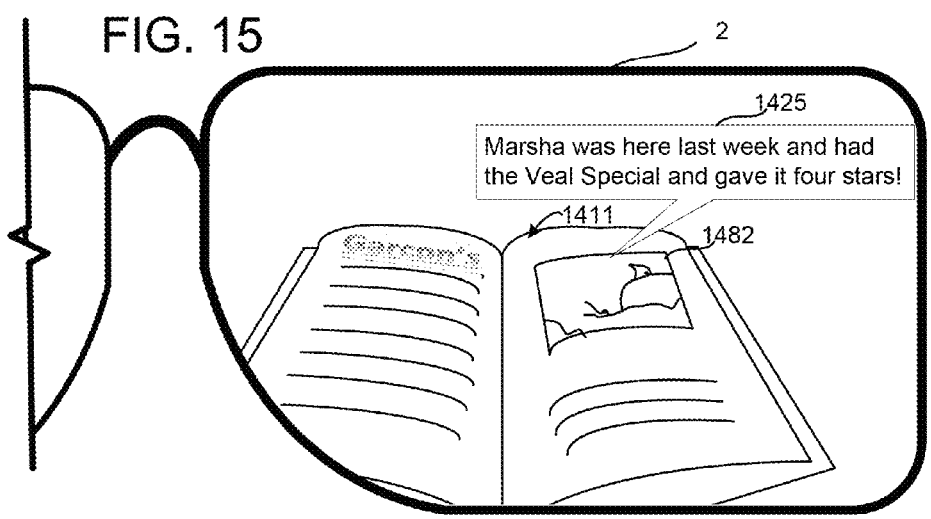

FIG. 15 is a similar view indicating the perspective of wearer showing feedback for social data which may be provided. A wearer of the device 2 viewing the same menu 1411 is provided with social feedback 1425 indicating that the wearer's friend "Marsha" has consumed the veal special last week and liked it. Location or other tagging associations can trigger social sharing information from the wearer's friend "Marsha".

FIG. 16 is similar view indicating feedback provided to the wearer based on the wearer's own historical data. In FIG. 16, the feedback 1510 indicates that the wearer did not like the veal special the last time the wearer ate at this particular restaurant.

FIG. 17 is an example of how consumption feedback can be provided to the wearer. In FIG. 17, the wearer is viewing a hamburger and the system indicates via a warning 1520 to the wearer that "this is your second big meal today; are you sure you want to do that" prompting the wearer to consider whether or not the wearer wishes to consume additional large mean since the system has tracked that fact that it has already consumed one large meal today.

FIG. 18 is a similar perspective illustrating feedback which may be provided to the wearer when the system cannot determine the type of food 1818 available in the field of view of the wearer. The prompt 1824 indicates that the system cannot determine the type of food and asks the wearer whether the wearer would like to identify it. The wearer can be provided with a selection menu as shown in FIG. 18 asking the wearer to select one of the various types of food the system had determined that the item is likely to be.

FIG. 19 illustrates an example of nutritional feedback where the system is not sure of the type of food item or the recipe which is being presented to the wearer. In this case, the wearer is presented with the system's "best guess" 1830 and a set of information indicating what a "typical" item of that type might have with respect to nutritional data. It should be understood that various examples illustrated herein are exemplary only, and a number of different types of feedback can be provided to the wearer, of varying detail, colors, sounds, and other information.

As noted above, the technology has been described with reference to use in providing feedback to a wearer in a situation involving the consumption of food items. It should be understood that the technology may be used in the preparation of meals. Where a user is preparing food items, ingredient data may be recognized and nutritional information provided to the wearer during the preparation process. Similarly, where the wearer is shopping for food, information may be provided to the wearer on choices of foods and nutritional information for specific items.

In addition, social information may be expanded to situations involving preparation of food. If, for example, one is preparing a meal for a social friend and shared information for that friend indicates food allergies or concerns, such feedback may be provided by the feedback application during the meal preparation process.

FIG. 20 is a block diagram of an exemplary mobile device which may operate in embodiments of the technology described herein (e.g. processing unit 4). Exemplary electronic circuitry of a typical mobile phone is depicted. The device 2000 includes one or more microprocessors 2012, and memory 2010 (e.g., non-volatile memory such as ROM and volatile memory such as RAM) which stores processor-readable code which is executed by one or more processors of the control processor 2012 to implement the functionality described herein.

Mobile device 2000 may include, for example, processors 2012, memory 2050 including applications and non-volatile storage. The processor 2012 can implement communications, as well as any number of applications, including the interaction applications discussed herein. Memory 2050 can be any variety of memory storage media types, including non-volatile and volatile memory. A device operating system handles the different operations of the mobile device 2000 and may contain wearer interfaces for operations, such as placing and receiving phone calls, text messaging, checking voicemail, and the like. The applications 2030 can be any assortment of programs, such as a camera application for photos and/or videos, an address book, a calendar application, a media player, an Internet browser, games, other multimedia applications, an alarm application, other third party applications, the interaction application discussed herein, and the like. The non-volatile storage component 2040 in memory 2010 contains data such as web caches, music, photos, contact data, scheduling data, and other files.

The processor 2012 also communicates with RF transmit/receive circuitry 2006 which in turn is coupled to an antenna 2002, with an infrared transmitted/receiver 2008, with any additional communication channels 2060 like Wi-Fi or Bluetooth, and with a movement/orientation sensor 2014 such as an accelerometer. Accelerometers have been incorporated into mobile devices to enable such applications as intelligent wearer interfaces that let wearers input commands through gestures, indoor GPS functionality which calculates the movement and direction of the device after contact is broken with a GPS satellite, and to detect the orientation of the device and automatically change the display from portrait to landscape when the phone is rotated. An accelerometer can be provided, e.g., by a micro-electromechanical system (MEMS) which is a tiny mechanical device (of micrometer dimensions) built onto a semiconductor chip. Acceleration direction, as well as orientation, vibration and shock can be sensed. The processor 2012 further communicates with a ringer/vibrator 2016, a wearer interface keypad/screen, biometric sensor system 2018, a speaker 2020, a microphone 2022, a camera 2024, a light sensor 2026 and a temperature sensor 2028.

The processor 2012 controls transmission and reception of wireless signals. During a transmission mode, the processor 2012 provides a voice signal from microphone 2022, or other data signal, to the RF transmit/receive circuitry 2006. The transmit/receive circuitry 2006 transmits the signal to a remote station (e.g., a fixed station, operator, other cellular phones, etc.) for communication through the antenna 2002. The ringer/vibrator 2016 is used to signal an incoming call, text message, calendar reminder, alarm clock reminder, or other notification to the wearer. During a receiving mode, the transmit/receive circuitry 2006 receives a voice or other data signal from a remote station through the antenna 2002. A received voice signal is provided to the speaker 2020 while other received data signals are also processed appropriately.

Additionally, a physical connector 2088 can be used to connect the mobile device 2000 to an external power source, such as an AC adapter or powered docking station. The physical connector 2088 can also be used as a data connection to a computing device. The data connection allows for operations such as synchronizing mobile device data with the computing data on another device.

A GPS transceiver 2065 utilizing satellite-based radio navigation to relay the position of the wearer applications is enabled for such service.

Figure 21:
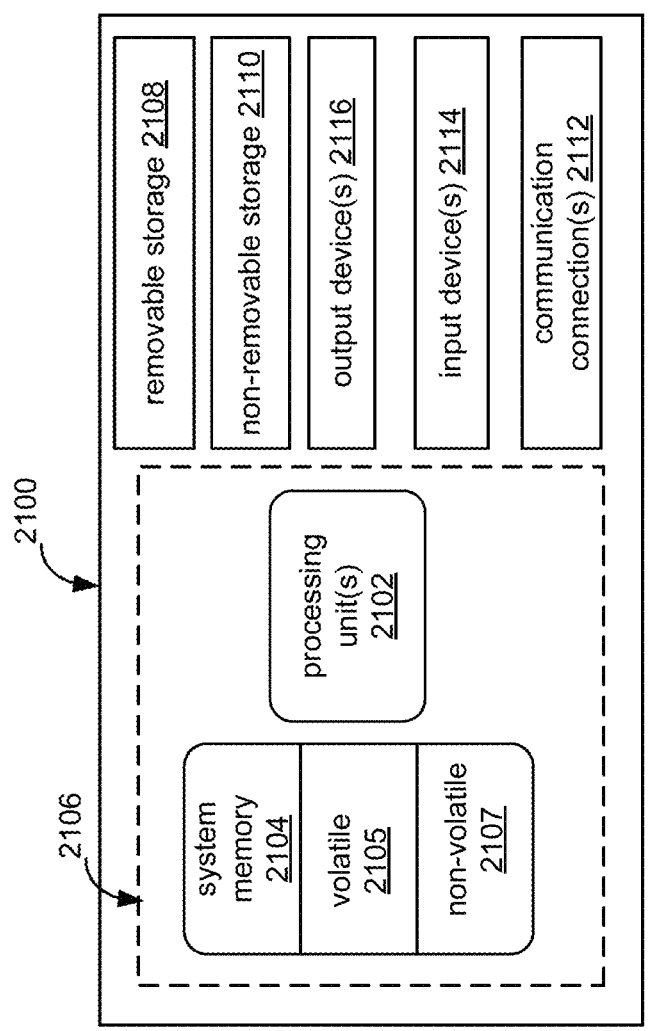
FIG. 21 is a block diagram of another exemplary processing device.

FIG. 21 is a block diagram of one embodiment of a computing system that can be used to implement a network accessible computing system or a companion processing module. FIG. 21 is a block diagram of one embodiment of a computing system that can be used to implement one or more network accessible computing systems 871 or a processing unit 4 which may host at least some of the software components of computing environment depicted in FIG. 8. With reference to FIG. 21, an exemplary system includes a computing device, such as computing device 2100. In its most basic configuration, computing device 2100 typically includes one or more processing units 2102 including one or more central processing units (CPU) and one or more graphics processing units (GPU). Computing device 2100 also includes memory 2104. Depending on the exact configuration and type of computing device, memory 2104 may include volatile memory 2105 (such as RAM), non-volatile memory 2107 (such as ROM, flash memory, etc.) or some combination of the two. This most basic configuration is illustrated in FIG. 21 by dashed line 2106. Additionally, device 2100 may also have additional features/functionality. For example, device 2100 may also include additional storage (removable and/or non-removable) including, but not limited to, magnetic or optical disks or tape. Such additional storage is illustrated in FIG. 16 by removable storage 2108 and non-removable storage 2110.

Device 2100 may also contain communications connection(s) 2112 such as one or more network interfaces and transceivers that allow the device to communicate with other devices. Device 2100 may also have input device(s) 2114 such as keyboard, mouse, pen, voice input device, touch input device, etc. Output device(s) 2116 such as a display, speakers, printer, etc. may also be included. All these devices are well known in the art and are not discussed at length here.

The example computer systems illustrated in the figures include examples of computer readable storage devices. A computer readable storage device is also a processor readable storage device. Such devices may include volatile and non-volatile, removable and non-removable memory devices implemented in any method or technology for storage of information such as computer readable instructions, data structures, program modules or other data. Some examples of processor or computer readable storage devices are RAM, ROM, EEPROM, cache, flash memory or other memory technology, CD-ROM, digital versatile disks (DVD) or other optical disk storage, memory sticks or cards, magnetic cassettes, magnetic tape, a media drive, a hard disk, magnetic disk storage or other magnetic storage devices, or any other device which can be used to store the desired information and which can be accessed by a computer Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An augmented display apparatus, comprising:
a see-through, head mounted display;
a plurality of sensors detecting visual information in a field of view of the apparatus;
one or more processing devices in communication with the see-through, head mounted display and the sensors, the one or more processing devices automatically
identify food items proximate to the apparatus;
track consumption of one or more of the food items of a wearer wearing the apparatus;
determine feedback information for the one or more of the food items identified and relevant to the wearer of the apparatus before consumption of one or more of the food items, the feedback information based on social feedback information for the food items from a social network provided by one or more friends of the wearer; and
render the feedback information as a virtual object, based on the social feedback information and prior to consumption, in the see-through, head mounted display.

2. The apparatus of claim 1 wherein the one or more processing devices determine nutritional information for the food items, and the feedback information includes nutritional information based on the consumption.

3. The apparatus of claim 1 wherein the one or more processing devices access image data to match sensor data to food types based on the image data and wherein the one or more processing devices nutritional data based on recipe data for identified food items.

4. The apparatus of claim 3 wherein the one or more processing devices access wearer profile information, and wherein the one or more processing devices identify the food items based on wearer consumption history.

5. The apparatus of claim 1 wherein the one or more processing devices access recipe information provided by a third party, and wherein the one or more processing devices provide nutritional feedback in the see-through, head mounted display based on said recipe information and the consumption.

6. The apparatus of claim 1 wherein the one or more processing devices access wearer profile information, and wherein the consumption data is recorded in the wearer profile information and incorporated into feedback information for subsequent consumption events.

7. The apparatus of claim 1 wherein the consumption is identified by detecting a wearer gesture of consumption.

8. The apparatus of claim 1 wherein the consumption is identified by detecting wearer consumption sounds.

9. The apparatus of claim 1 wherein feedback includes feedback on the food items by one or more friends of the wearer.

10. A see-through, head mounted display device including a processor and computer readable storage, the storage including computer readable instructions when executed by the processor performing a method comprising:
receiving input from a plurality of sensors mounted on the see-through, head mounted display device, the sensors mounted to detect image data in a field of view of the see-through, head mounted display device and wearer gaze of the see-through, head mounted display device;
identifying food items proximate to the see-through, head mounted device based on the image data and the wearer gaze;
accessing social feedback information for the one or more food items from a social network, the social feedback information based on social media information from one or more friends of a wearer concerning one or more of the food items identified;
detecting consumption of one or more of the food items identified and generating consumption feedback information for the one or more of the food items identified; and
providing the social feedback information and the consumption feedback information on the food items for display in the see-through, head mounted display device as virtual objects, each of the feedback information together identifiable with one or more of the food items.

11. The see-through, head mounted display device of claim 10 wherein the feedback information comprises one of:
nutritional information for the one or more food items;
wearer health information for the one or more food items; and
social friend recommendations concerning the one or more food items.

12. The see-through, head mounted display device of claim 10 wherein identifying comprises:
determining a location for the display device;
accessing food item data associated with the location;
evaluating the image data to determine food items based on the location and the food item data.

13. The see-through, head mounted display device of claim 12 wherein identifying comprises evaluating the image data and the wearer gaze to parse items on a menu associated with the location, matching items on the menu with the food item data associated with the location, and wherein providing feedback includes providing location specific feedback for the food items.

14. The see-through, head mounted display device of claim 10 wherein identifying comprises evaluating the image data and the wearer gaze matching items in the image data with data associated with known food on a menu with food item data associated with a location, and wherein providing feedback includes providing location specific feedback for the food items.

15. A method for providing nutritional feedback for food items in a field of view of a see-through, head mounted display system, comprising:
determining a location, orientation and the field of view for the see-through, head mounted display system;
determining whether third party data is available for the location and if so, associating the third party data with the location, the third party data including food identification data and nutritional information for food items from a social network;
evaluating sensor data from the see-through, head mounted display system to identify food items proximate to the system, the evaluating using the third party data acquired from the social network;
determining nutritional feedback information matching one or more of the food items identified and relevant to a wearer of the system;
detecting consumption of at least a portion of the one or more food items by the wearer; and
providing nutritional feedback based on the third party data for at least one of the food items and the consumption to the wearer in the see-through, head mounted display system as a virtual object.

16. The method of claim 15 wherein determining includes accessing user profile information determining one or more friends of the user, and further providing social feedback information to the wearer based on the one or more friends of the wearer.

17. The method of claim 16 wherein the evaluating includes matching food item data with sensor data to identify food items in the field of view.

18. The method of claim 17 wherein the determining includes matching estimated nutritional data with identified food items based on a determination of the food item.

19. The method of claim 18 further including detecting consumption by detecting a wearer gesture of consumption.

20. The method of claim 18 including detecting consumption by detecting a wearer sound of consumption.

* * * * *